(12) United States Patent
Bradley et al.

(10) Patent No.: US 12,142,355 B2
(45) Date of Patent: *Nov. 12, 2024

(54) HEALTH CARE INFORMATION SYSTEM PROVIDING STANDARDIZED OUTCOME SCORES ACROSS PATIENTS

(71) Applicant: OM1, Inc., Boston, MA (US)

(72) Inventors: Scott Bradley, North Reading, MA (US); Richard Gliklich, Weston, MA (US); Christopher Francois Paul, Lincoln, MA (US)

(73) Assignee: OM1, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/169,372

(22) Filed: Feb. 15, 2023

(65) Prior Publication Data

US 2023/0197224 A1 Jun. 22, 2023

Related U.S. Application Data

(63) Continuation of application No. 15/465,550, filed on Mar. 21, 2017, now Pat. No. 11,594,311.

(Continued)

(51) Int. Cl.
*G16H 10/60* (2018.01)
*G06F 17/11* (2006.01)
(Continued)

(52) U.S. Cl.
CPC .............. *G16H 10/60* (2018.01); *G06F 17/11* (2013.01); *G06N 20/00* (2019.01); *H04L 67/01* (2022.05)

(58) Field of Classification Search
CPC ........ G16H 10/60; G16H 50/20; G16H 50/30; G06F 17/11; G06F 17/18; G06N 20/00; H04L 67/01

See application file for complete search history.

(56) References Cited

U.S. PATENT DOCUMENTS

| 5,486,999 A | 1/1996 | Mebane |
| 5,508,912 A | 4/1996 | Schneiderman |

(Continued)

FOREIGN PATENT DOCUMENTS

| EP | 2 614 480 A2 | 7/2013 |
| WO | 00/57310 A1 | 9/2000 |

(Continued)

OTHER PUBLICATIONS

Voshaar et al., Calibration of the PROMIS Physical Function Item Bank in Dutch Patients with Rheumatoid Arthritis, Mar. 2014, PLOS ONE, vol. 9, Issue 3, pp. 1-11. (Year: 2014).*

(Continued)

*Primary Examiner* — Christopher L Gilligan
(74) *Attorney, Agent, or Firm* — Patent GC LLC; Peter Gordon

(57) ABSTRACT

Health care information for multiple patients is processed to classify patients into categories. Additional data fields related to a category in which a patient is classified are added to the patient record. These data fields are populated in part by automatically processing the existing patient data. Such automatic processing can result in a probability that the underlying data supports having a particular value stored in one of the added data fields, and this probability also can be stored. Over time, additional data can be obtained from patients, caregivers and other sources, for structured data fields based on data entry forms for patient reported outcomes, caregiver reported outcomes, events of interest, survival and resource utilization. A set of factor scores is computed for each patient, for each category in which the patient is classified. An outcome score is computed for each patient for each category in which the patient is classified, using an outcome function defined for that category, as a weighted function of one or more of the factor scores. The (Continued)

outcome function for a category is standardized across all patients classified in that category.

20 Claims, 17 Drawing Sheets

Related U.S. Application Data

(60) Provisional application No. 62/315,885, filed on Mar. 31, 2016.

(51) Int. Cl.
  *G06N 20/00* (2019.01)
  *H04L 67/01* (2022.01)

(56) References Cited

U.S. PATENT DOCUMENTS

| | | | |
|---|---|---|---|
| 5,619,421 A | 4/1997 | Venkataraman et al. | |
| 5,961,332 A | 10/1999 | Joao | |
| 6,101,511 A | 8/2000 | Derose et al. | |
| 6,317,731 B1 | 11/2001 | Luciano | |
| 6,524,241 B2 | 2/2003 | Iliff | |
| 6,687,685 B1 | 2/2004 | Sadeghi et al. | |
| 7,076,437 B1 | 7/2006 | Levy | |
| 7,194,301 B2 | 3/2007 | Jenkins et al. | |
| 7,433,519 B2 | 10/2008 | Rynderman | |
| 7,739,126 B1 | 6/2010 | Cave et al. | |
| 7,809,660 B2 | 10/2010 | Friedlander et al. | |
| 7,916,363 B2 | 3/2011 | Rynderman | |
| 7,930,262 B2 | 4/2011 | Friedlander et al. | |
| 7,949,620 B2 | 5/2011 | Otte et al. | |
| 8,090,590 B2 | 1/2012 | Fotsch et al. | |
| 8,140,541 B2 | 3/2012 | Koss | |
| 8,154,776 B2 | 4/2012 | Rynderman | |
| 8,165,973 B2 | 4/2012 | Alexe et al. | |
| 8,311,849 B2 | 11/2012 | Soto et al. | |
| 8,335,698 B2 | 12/2012 | Angell et al. | |
| 8,392,215 B2 | 3/2013 | Tawil | |
| 8,538,773 B2 | 9/2013 | Eddy et al. | |
| 8,560,281 B2 | 10/2013 | Spertus et al. | |
| 8,583,586 B2 | 11/2013 | Ebadollahi et al. | |
| 8,930,223 B2 | 1/2015 | Friedlander et al. | |
| 9,514,416 B2 | 12/2016 | Lee et al. | |
| 9,646,271 B2 | 5/2017 | Friedlander et al. | |
| 9,690,844 B2 | 6/2017 | Mukherjee et al. | |
| 10,061,812 B2 | 8/2018 | Marshall et al. | |
| 10,282,512 B2 * | 5/2019 | Bennett | G16H 50/20 |
| 10,311,363 B1 | 6/2019 | Florissi et al. | |
| 10,311,975 B2 * | 6/2019 | Young | G16H 50/30 |
| 10,706,329 B2 | 7/2020 | Anushiravani et al. | |
| 10,731,223 B2 | 8/2020 | Kennedy et al. | |
| 10,731,233 B2 | 8/2020 | Yamada et al. | |
| 11,257,574 B1 | 2/2022 | Boussios et al. | |
| 11,527,326 B2 | 12/2022 | McNair et al. | |
| 11,594,310 B1 | 2/2023 | Bradley et al. | |
| 11,594,311 B1 | 2/2023 | Bradley et al. | |
| 11,862,346 B1 | 1/2024 | Boussios et al. | |
| 11,967,428 B1 | 4/2024 | Boussios et al. | |
| 12,057,204 B2 | 8/2024 | Bradley et al. | |
| 2003/0014284 A1 | 1/2003 | Jones | |
| 2004/0122706 A1 | 6/2004 | Walker et al. | |
| 2004/0122707 A1 | 6/2004 | Sabol et al. | |
| 2004/0243362 A1 | 12/2004 | Liebman | |
| 2006/0058384 A1 | 3/2006 | Hogg | |
| 2006/0129427 A1 | 6/2006 | Wennberg | |
| 2006/0129428 A1 | 6/2006 | Wennberg | |
| 2006/0173663 A1 | 8/2006 | Langheier et al. | |
| 2007/0021979 A1 | 1/2007 | Cosentino et al. | |
| 2007/0172907 A1 | 7/2007 | Volker et al. | |
| 2007/0255113 A1 | 11/2007 | Grimes | |
| 2008/0171916 A1* | 7/2008 | Feder | G16H 50/20 |
| | | | 600/300 |
| 2008/0208813 A1 | 8/2008 | Friedlander et al. | |
| 2008/0235049 A1 | 9/2008 | Morita et al. | |
| 2008/0294459 A1 | 11/2008 | Angell et al. | |
| 2009/0119337 A1 | 5/2009 | Biedermann | |
| 2009/0164237 A1 | 6/2009 | Hunt et al. | |
| 2009/0259494 A1 | 10/2009 | Feder et al. | |
| 2009/0287503 A1 | 11/2009 | Angell et al. | |
| 2010/0021956 A1 | 1/2010 | Shearer et al. | |
| 2010/0191088 A1 | 7/2010 | Anderson et al. | |
| 2010/0240035 A1 | 9/2010 | Jablons et al. | |
| 2010/0324927 A1 | 12/2010 | Tinsley | |
| 2011/0010328 A1 | 1/2011 | Patel et al. | |
| 2011/0071363 A1 | 3/2011 | Montijo et al. | |
| 2011/0106558 A1 | 5/2011 | Solito et al. | |
| 2011/0125680 A1 | 5/2011 | Bosworth et al. | |
| 2011/0177956 A1 | 7/2011 | Korenberg | |
| 2011/0288877 A1 | 11/2011 | Ofek et al. | |
| 2012/0065987 A1 | 3/2012 | Farooq et al. | |
| 2012/0084064 A1 | 4/2012 | Dzenis et al. | |
| 2012/0110016 A1 | 5/2012 | Phillips | |
| 2012/0179478 A1 | 7/2012 | Ross | |
| 2012/0191640 A1 | 7/2012 | Ebadollahi et al. | |
| 2012/0215560 A1 | 8/2012 | Ofek et al. | |
| 2012/0254098 A1 | 10/2012 | Flinn et al. | |
| 2012/0296675 A1 | 11/2012 | Silverman | |
| 2013/0185231 A1 | 7/2013 | Baras et al. | |
| 2014/0006447 A1 | 1/2014 | Friedlander et al. | |
| 2014/0074510 A1 | 3/2014 | Mcclung et al. | |
| 2014/0081898 A1 | 3/2014 | Saigal et al. | |
| 2014/0095204 A1 | 4/2014 | Fung et al. | |
| 2014/0108044 A1 | 4/2014 | Reddy et al. | |
| 2014/0164022 A1 | 6/2014 | Reed et al. | |
| 2014/0249834 A1 | 9/2014 | D'Souza et al. | |
| 2014/0350954 A1 | 11/2014 | Ellis et al. | |
| 2015/0106109 A1 | 4/2015 | Crowley et al. | |
| 2015/0106115 A1 | 4/2015 | Hu et al. | |
| 2015/0235001 A1 | 8/2015 | Fouts | |
| 2015/0339442 A1 | 11/2015 | Oleynik | |
| 2015/0347599 A1 | 12/2015 | Mcmains et al. | |
| 2016/0004840 A1 | 1/2016 | Rust et al. | |
| 2016/0012202 A1 | 1/2016 | Hu et al. | |
| 2016/0015347 A1 | 1/2016 | Bregman-Amitai et al. | |
| 2016/0029919 A1 | 2/2016 | Hebert et al. | |
| 2016/0078183 A1 | 3/2016 | Trygstad et al. | |
| 2016/0120481 A1 | 5/2016 | Li et al. | |
| 2016/0188814 A1 | 6/2016 | Raghavan et al. | |
| 2016/0188834 A1 | 6/2016 | Erdmann et al. | |
| 2016/0196394 A1 | 7/2016 | Chanthasiriphan et al. | |
| 2016/0235373 A1 | 8/2016 | Sharma et al. | |
| 2016/0283679 A1 | 9/2016 | Hu et al. | |
| 2016/0283686 A1 | 9/2016 | Hu et al. | |
| 2016/0354039 A1 | 12/2016 | Soto et al. | |
| 2017/0046602 A1 | 2/2017 | Hu et al. | |
| 2017/0061093 A1 | 3/2017 | Amarasingham et al. | |
| 2017/0124263 A1* | 5/2017 | Crafts, Jr. | G16H 70/20 |
| 2017/0124279 A1* | 5/2017 | Rothman | G16H 50/30 |
| 2017/0147777 A1 | 5/2017 | Kim et al. | |
| 2017/0235887 A1 | 8/2017 | Cox et al. | |
| 2017/0262609 A1* | 9/2017 | Perlroth | G16H 10/60 |
| 2017/0323075 A1 | 11/2017 | Krause et al. | |
| 2018/0268937 A1 | 9/2018 | Spetzler et al. | |
| 2018/0330805 A1 | 11/2018 | Cheung et al. | |
| 2018/0336319 A1 | 11/2018 | Itu et al. | |
| 2019/0079938 A1 | 3/2019 | Agrawal et al. | |
| 2021/0098090 A1 | 4/2021 | Thomas et al. | |
| 2022/0148695 A1 | 5/2022 | Boussios et al. | |
| 2023/0197223 A1 | 6/2023 | Bradley et al. | |
| 2024/0096500 A1 | 3/2024 | Boussios et al. | |
| 2024/0153647 A1 | 5/2024 | Boussios et al. | |

FOREIGN PATENT DOCUMENTS

| | | | |
|---|---|---|---|
| WO | 0209004 A1 | 1/2002 | |
| WO | 02/09580 A1 | 2/2002 | |
| WO | 03/104939 A2 | 12/2003 | |
| WO | 2006/086181 A1 | 8/2006 | |
| WO | 2007/050147 A1 | 5/2007 | |
| WO | 2008/048662 A2 | 4/2008 | |
| WO | WO-2008079341 A2 * | 7/2008 | G06F 19/327 |
| WO | 2012019000 A2 | 2/2012 | |

(56) References Cited

FOREIGN PATENT DOCUMENTS

| WO | 2012/033771 | A2 | | 3/2012 | |
| WO | 2014/028541 | A1 | | 2/2014 | |
| WO | WO-2015169810 | A1 | * | 11/2015 | ......... G06F 19/3431 |

OTHER PUBLICATIONS

Awan, et al., "Machine Learning-Based Prediction of Heart Failure Readmission or Death: Implications of Choosing the Right Model and the Right Metrics", ESC Heart Failure, DOI: 10.1002/ehf2. 12419, vol. 6, Feb. 27, 2019, pp. 428-435.

Bertens, et al., "A nomogram was developed to enhance the use of multinomial logistic regression modeling in diagnostic research", Journal of Clinical Epidemiology, vol. 71, Mar. 2016, pp. 51-57.

Bodhe, et al., "A Proposed Mobile Based Health Care System for Patient Diagnosis using Android OS", International Journal of Computer Science and Mobile Computing, vol. 3, Issue 5, May 2014, pp. 422-427.

Cheng, et al., "Risk Prediction with Electronic Health Records: A Deep Learning Approach", Proceedings of the SIAM International Conference on Data Mining, Jun. 2016, pp. 432-440.

Clockbackward, "Ordinary Least Squares Linear Regression: Flaws, Problems and Pitfalls", Jun. 18, 2009, 16 pages.

Grossman, et al., "Learning Bayesian Network Classifiers by Maximizing Conditional Likelihood", Proceedings of the 21st International Conference on Machine Learning, 2004, 8 pages.

Hileman, et al., "Accuracy of Claims-Based Risk Scoring Models", Society of Actuaries, Oct. 2016, pp. 1-90.

Mccarthy, et al., "The Estimation of Sensitivity and Specificity of Clustered Binary Data", Statistics and Data Analysis, SUGI 31, Paper 206-31, 2006, 10 pages.

Mojsilovic, et al., "Semantic based categorization, browsing and retrieval in medical image databases", Proceedings of the International Conference on Image Processing, IEEE, 2002, pp. 145-148.

Pearson, et al., "Disease Progression Modeling from Historical Clinical Databases", Proceedings of the Eleventh ACM SIGKDD International Conference on Knowledge Discovery in Data Mining, Aug. 21-24, 2005, pp. 788-793.

Ribeiro, et al. "Why Should I Trust You?", Explaining the Predictions of Any Classifier, DOI: http://dx.doi.org/10.1145/2939672. 2939778, 2016, pp. 1135-1144.

Schneider, "Enabling Advanced Analytics to Improve Outcomes", Truven Health Analytics, Aug. 23, 2012, pp. 1-46.

Shen, "Using Cluster Analysis, Cluster Validation, and Consensus Clustering to Identify Subtypes of Pervasive Developmental Disorders", Nov. 2007, 119 pages.

Soni, et al., "Using Associative Classifiers for Predictive Analysis in Health Care Data Mining", International Journal of Computer Applications, vol. 4, No. 5, Jul. 2010, pp. 33-37.

Su, et al., "Using Bayesian Networks to Discover Relations Between Genes, Environment, and Disease", Bio Data Mining, http://www.biodatamining.org/content/6/1/6, 2013, 21 pages.

Suo, et al., "Risk Factor Analysis Based on Deep Learning Models", Proceedings of the 7th ACM International Conference on Bioinformatics, Computational Biology, and Health Informatics, Oct. 2-5, 2016, 10 pages.

Tan, et al., "Cluster Analysis: Basic Concepts and Algorithms", Introduction to Data Mining (Second Edition), Chapter 8, Feb. 2018, pp. 487-568.

Truven Health Analytics, "Flexible Analytics for Provider Evaluation", Solution Spotlight, 2017, 4 pages.

Truven Health Analytics, "Modeling Studies: Published Articles and Presentations", 2016, pp. 1-6.

Truven Health Groups, "Enterprise Decision Support", Product Spotlight, 2012, 2 pages.

U.S. Patent and Trademark Office, "Final Office Action Received", U.S. Appl. No. 16/724,264, Nov. 30, 2022, 11 pages.

U.S. Patent and Trademark Office, "Final Office Action Received", U.S. Appl. No. 15/465,542, Dec. 30, 2019, 54 pages.

U.S. Patent and Trademark Office, "Final Office Action Received", U.S. Appl. No. 15/465,542, Jan. 4, 2022, 60 pages.

U.S. Patent and Trademark Office, "Final Office Action Received", U.S. Appl. No. 15/465,550, Mar. 21, 2022, 12 pages.

U.S. Patent and Trademark Office, "Final Office Action Received", U.S. Appl. No. 16/386,123, Mar. 31, 2023, 59 pages.

U.S. Patent and Trademark Office, "Final Office Action Received", U.S. Appl. No. 15/927,766, Oct. 6, 2020, 22 pages.

U.S. Patent and Trademark Office, "Final Office Action Received", U.S. Appl. No. 15/465,550, Oct. 14, 2020, 15 pages.

U.S. Patent and Trademark Office, "Non Final Office Action Received", U.S. Appl. No. 16/386,123, Jun. 28, 2022, 55 pages.

U.S. Patent and Trademark Office, "Non Final Office Action Received", U.S. Appl. No. 15/927,766, Apr. 30, 2020, 19 pages.

U.S. Patent and Trademark Office, "Non Final Office Action Received", U.S. Appl. No. 15/465,550, Jun. 26, 2019, 8 pages.

U.S. Patent and Trademark Office, "Non Final Office Action Received", U.S. Appl. No. 15/465,550, Mar. 13, 2020, 12 pages.

U.S. Patent and Trademark Office, "Non Final Office Action Received", U.S. Appl. No. 15/465,542, Mar. 19, 2019, 29 pages.

U.S. Patent and Trademark Office, "Non-Final Office Action Received", U.S. Appl. No. 15/465,542, Apr. 1, 2021, 73 pages.

U.S. Patent and Trademark Office, "Non-Final Office Action Received", U.S. Appl. No. 15/465,550, Jul. 29, 2021, 31 pages.

U.S. Patent and Trademark Office, "Non-Final Office Action Received", U.S. Appl. No. 16/724,264, Mar. 21, 2022, 20 pages.

U.S. Patent and Trademark Office, "Notice of Allowance Received", U.S. Appl. No. 15/465,542, Oct. 28, 2022, 12 pages.

U.S. Patent and Trademark Office, "Notice of Allowance Received", U.S. Appl. No. 15/465,550, Aug. 16, 2022, 8 pages.

U.S. Patent and Trademark Office, "Notice of Allowance Received", U.S. Appl. No. 15/465,542, Aug. 24, 2022, 11 pages.

U.S. Patent and Trademark Office, "Notice of Allowance Received", U.S. Appl. No. 16/724,264, Sep. 6, 2023, 7 pages.

U.S. Patent and Trademark Office, "Notice of Allowance Received", U.S. Appl. No. 15/465,550, Jan. 26, 2023, 8 pages.

U.S. Patent and Trademark Office, "Notice of Allowance Received", U.S. Appl. No. 16/724,264, May 22, 2023, 8 pages.

U.S. Patent and Trademark Office, "Notice of Allowance Received", U.S. Appl. No. 15/927,766, Oct. 14, 2021, 35 pages.

U.S. Patent and Trademark Office, "Restriction Requirement Received", U.S. Appl. No. 16/724,264, Oct. 7, 2021, 6 pages.

Dua, et al., "Machine learning in healthcare informatics", vol. 56. Berlin: Springer, 2014, 334 pages.

U.S. Patent and Trademark Office, "Non-Final Office Action Received", U.S. Appl. No. 18/169,363, Jul. 7, 2023, 48 pages.

U.S. Patent and Trademark Office , "Final Office Action Received", U.S. Appl. No. 18/414,296, Jul. 10, 2024, 11 Pages.

U.S. Patent and Trademark Office , "Non-Final Office Action Received", U.S. Appl. No. 18/414,296, Mar. 22, 2024, 13 Pages.

U.S. Patent and Trademark Office , "Notice of Allowance Received", U.S. Appl. No. 16/386,123, Dec. 13, 2023, 12 Pages.

U.S. Patent and Trademark Office , "Notice of Allowance Received", U.S. Appl. No. 18/169,363, Mar. 27, 2024, 10 Pages.

* cited by examiner

Patient record 700
    Patient ID
    Base field 702-1
        key 704
        value 706
    ...
    Base field 702-X
        name 708
        unstructured text 710

Category field 712-1
        category ID 714
        probability 716
        other data 718
    ...
    Category field 712-N
        . . .
    Additional structured field 720-1
        key 722
        value 724
        probability 726
        date/time 728
    ...
    Additional structured field 720-Y
        ...
    Outcome data 730-1
        category ID 732
        date/time 734
        patient reported outcome measure 736
        clinical response measure 738
        events of interest measure 740
        survival 742
        resource cost measure 744
        outcome score 746
    ...
    Outcome data 730-N
        ...

FIG. 7

Thanks for completing the survey!

Up 24 since Dec. 31, 2015

My Programs
Hospital Network
Show: Percentage Active     6 month trailing average
Cardiology Progam     ⌒1500
4 Modules
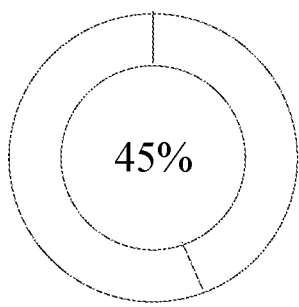
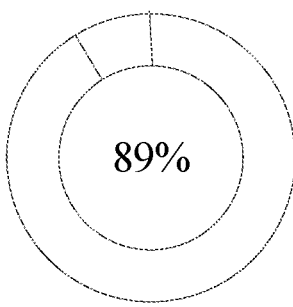
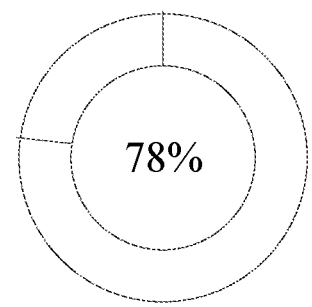
Ischemic Heart Disease   Hypertensive Heart...   Valvular Heart Disease
152 Active Patients      1239 Active Patients    1349 Active Patients
FIG. 15

HEALTH CARE INFORMATION SYSTEM PROVIDING STANDARDIZED OUTCOME SCORES ACROSS PATIENTS

CROSS-REFERENCE TO RELATED APPLICATIONS

This application is a non-provisional application claiming priority to prior file provisional application Ser. No. 62/315,885, filed Mar. 31, 2016, entitled "HEALTH CARE INFORMATION SYSTEM PROVIDING STANDARDIZED OUTCOME SCORES ACROSS PATIENTS", which is hereby incorporated by reference.

BACKGROUND

A challenge in the health care industry is providing meaningful data, on a regular basis, to health care providers, patients, and others, regarding health care outcomes of patients.

Currently, health care outcomes typically are measured as part of specifically designed health programs, such as health outcomes measurement programs or other clinical programs or clinical trials or clinical studies, which include a select group of patients. A health program involves the systematic collection and analysis of data from multiple patients about the patients' medical conditions and demographics, interventions for those patients, and changes in patients' health status, to determine how changes in health status can be related to the medical conditions, demographics and interventions. Patients first are qualified to participate in such a health program, and then consent to participation, before their data can be used in the health program.

The selection criteria for these health programs are not readily available to health care providers of the patients, making it difficult for health care providers to identify patients who would qualify. Further, even if a health care provider, or the patient, were aware that a patient would qualify for a health program, there is significant labor involved in processing forms and other instruments to initiate the patient's participation in the health program.

Such health programs also rely on systematic data collection to provide information useful for computing health care outcomes. Even if a patient has been selected for and enrolled in a health program, data available from various medical records or other health related records for that patient can be incomplete or inaccurate. In current practice, systematic data collection is performed by the health program by having experts review and process available data into consistent formats, and/or by having health care providers perform data entry in response to questionnaires. The collected data can be either structured or unstructured data.

As a result, current practices limit both the quantity and quality of data available for computing and delivering information about health care outcomes. Additionally, even with satisfactory data collection, healthcare outcomes are not standardized for a given condition. In other words, there is no standardized framework for reporting healthcare outcomes across a set of patients outside of a specific health program. Thus, when outcomes are reported, they generally are reported as individual metrics or composites relevant within a specific health program. Such measures of healthcare outcomes also do not provide good insights into actionable interventions and treatments that could help patients and their health care providers improve the outcomes of their care, or current risks presented by patients with their current conditions.

SUMMARY

This Summary introduces a selection of concepts, in simplified form, which are described further in the Detailed Description below. This Summary is intended neither to identify key or essential features, nor to limit the scope, of the claimed subject matter.

A computer system processes health care information for multiple patients to classify patients into categories. A category generally is related to a specific medical condition. The computer system can automatically enroll a patient in any health program associated with the category in which the patient is classified. The computer system can add, to the patient record for a patient, one or more additional data fields related to a category in which the patient is classified. An additional data field can be a structured data field or an unstructured data field. The computer system can populate the additional data fields with values, at least in part, by automatically processing the existing patient data. Such automatic processing can result in a probability that the underlying data supports having a particular value stored in one of the additional data fields. The computer system also can store, in association with a particular value for a data field, data indicating this probability.

Over time, additional data can be obtained from patients, caregivers and other sources. The computer system can continue to update the patient data, for example by updating existing data fields, adding further data fields, and updating additional data fields and related probabilities. Such additional data can be based on, for example, data entry forms for patient reported outcomes, clinical response measures, events of interest, survival and resource utilization.

The computer system also computes a set of factor scores for each patient, for each category in which the patient is classified. Such factor scores can include values for a patient reported measurement, a clinical response measurement, and one or more of an events of interest measurement, a survival measurement and a resource utilization measurement. The factor scores can be computed using functions defined for the category in which the patient is classified. The computer system computes an outcome score for each patient for each category in which the patient is classified, using an outcome function defined for that category. The outcome function for a category is a weighted function of one or more factor scores computed for that category. The outcome function for a category is standardized across all patients classified in that category.

More particularly, a healthcare information system includes a plurality of classifiers which process health care information related to patients to determine a likelihood that a patient belongs in a category. A classifier is defined for each category. A category is associated with a medical condition or procedure and an outcome function with which outcome scores are to be measured and tracked for patients in that category. The health care information system includes a training process that implements machine learning techniques to train the classifiers given training sets. After training, the classifier determines a likelihood that a patient has a condition corresponding to the classifier by processing the health care information of the patient. For each classifier, the health care information system can store data over time for each patient, indicating whether the patient is likely in the category represented by the classifier.

The training process can use a variety of techniques to preprocess the training set to improve the quality of the resulting classifiers. For example, the training process can apply natural language processing techniques to patient data from training sets to generate additional features for training. The training process may perform various normalization or filtering operations to ensure data is consistent across records and with a patient record. Patient data also can be processed using a variety of techniques, such as deep learning models, to identify pertinent features in the patient data.

One or more additional data fields can be associated with a category. For example, if the category is associated with a specific health program, the additional data fields can include any data fields for which data is collected as part of that health program. After a patient is classified in a category, the health care information system adds the additional data fields for that category to the patient record. The additional data fields added to the patient record can be structured to store a value and a probability indicative of a level of certainty about that value.

The health care information system can populate the additional data fields, or any other data field missing a value, with values, and optionally probabilities for those values, in a number of ways. For example, the health care information system can derive values for the additional data fields for a patient from existing health care information for the patient. A function can be associated with the data field to define how to derive the value for the data field as a function of other patient data. As another example, the health care information system can prompt a user to enter data, such as by presenting a form to be completed by a patient or a health care provider. The health care information system can be configured to derive a value for a data field probabilistically, using one or more classifiers, which in turn provides both a value and a probability associated with that value to be stored for the data field.

The category in which a patient is classified may be associated with a specific health program, such as a health outcomes measurement program, or a clinical program, or a clinical trial or a clinical study. If the probability that a patient is classified in a category exceeds a threshold, then the health care information system can initiate an automatic enrollment process to enroll the patient in the health program associated with that category. In some instances, the additional data fields added to the patient data are specified by the health program, and the automatic enrollment process adds these data fields to the patient record. The automatic enrollment process also can specify data entry forms to be presented to the patient on a regular basis to provide for further structured data collection.

The health care information system also includes an outcome function for each category for computing an outcome score for patients in that category. The outcome function for a condition for a patient is a weighted function of scores based on one or more factors, such as patient reported outcomes, clinical response indicators, survival, events of interest and resource consumption. That is, given a score for one or more factors for a condition for a patient, based on that patient's data, the health care information system computes a weighted function of these scores to compute the outcome score. The set of weights used to compute the outcome score for a condition for a patient is the same across all patients with the same condition. The health care information system can be programmed to allow the set of weights to be changed. The ability to make such changes also allows for analysis of how outcome scores are affected by different weights.

The health care information system periodically computes health care outcomes for each patient, for each condition which the patient has, i.e., for each category in which that patient is classified. At any given time point in an historical patient record, the health care information system can compute an outcome score for the condition for the patient. The health care information system can compute the outcome score for a condition for a patient at many points in time, over time. A patient can have multiple conditions for which the health care information system separately computes health care outcomes.

A graphical user interface of the health care information system presents, for each patient, the outcome score for a selected condition for the patient, whether at a current point in time, a past point in time or over a period of time. The graphical user interface can present information about how the outcome score is computed, based on the weighting function and the underlying scores for different factors.

The health care information system also can provide information about risks associated with a patient. For example, for each category, known risks can have an associated data field for which the value, a probability, is determined using an associated classifier. The classifier uses a predictive model to determine a probability or risk that a patient will experience a particular condition or event given that patient's current data. Data about such risks also can be presented as part of the graphical user interface. Such risks also may be directly related to, i.e., a function of, some patient data or a factor score or outcome score for the patient.

In the following Detailed Description, reference is made to the accompanying drawings which form a part of this disclosure. These drawings show, by way of illustration, example implementations. Other implementations can be made without departing from the scope of this disclosure.

BRIEF DESCRIPTION OF THE DRAWINGS

FIG. 7 is an illustrative example implementation of data structures.

FIG. 15 is an example graphical user interface for use on a client computer to provide an administrator's dashboard.

DETAILED DESCRIPTION

Figure 1:
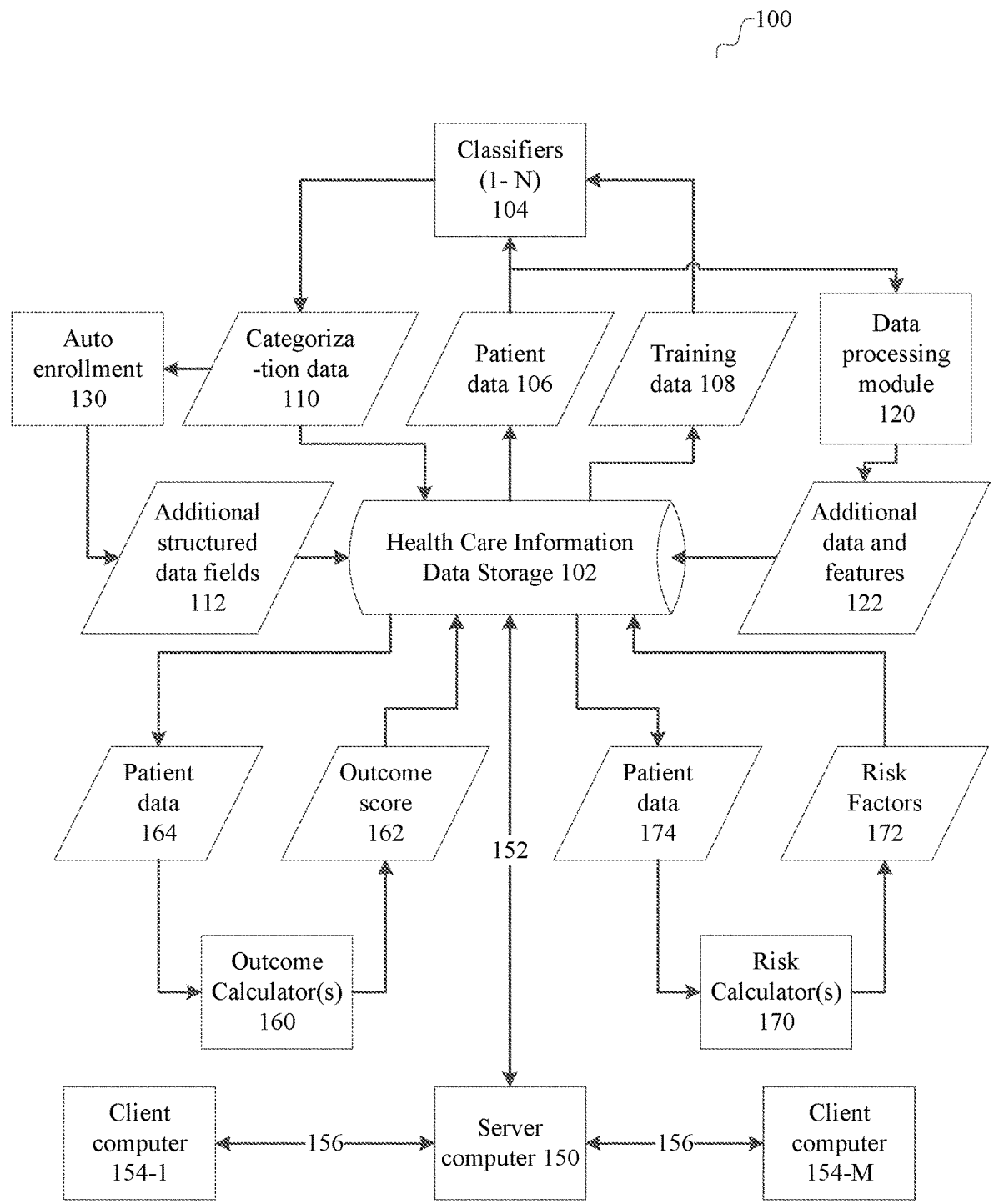
FIG. 1 is a block diagram of an example computer system supporting a health care information system providing standardized outcome scores across patients.

Referring to FIG. 1, a block diagram of an example implementation of a computer system supporting a health care information system will now be described.

A computer system 100 as shown in FIG. 1 includes health care information data storage 102 which stores health care information for a plurality of patients. The health care information for a patient can be obtained from a number of different sources of health care information for the patient including electronic medical records from the patient's health care providers, insurance providers and other sources.

More particularly, health care information can include, but is not limited to, information recorded for patients by a health care provider. Examples of health care providers include, but are not limited to, individuals, such as a physician, a therapist, a nurse, or support staff, and organizations, such a hospital or other facility employing health care providers. Health care information can include information from entities other than health care providers but who are otherwise involved in health care, such as insurers, laboratories, supply providers and the like, which may store information about claims, diagnostic tests, laboratory work, supplies and vendors. Health care information can include information reported by patients and/or their caregivers.

Such health care information generally includes demographic information and medical information.

The demographic information can include, for example, age, gender, race, family history, social history, and other information for the patient. If personally identified information authorized and stored, such information can include a name, an address and various contact information.

The medical information can include, for example, information about reported or observed symptoms of the patient, diagnoses made by the health care provider, any medications, treatments and other interventions prescribed or recommended by the health care provider, and/or any requests for laboratory work or diagnostic tests, and related reports or results. Such data can be stored as a history of interactions with the health care provider and may have multiple instances of a type of data over time, such as vital signs and lab results. Such data typically includes information, typically representing symptoms, diagnoses, procedures and medications, which is typically coded according to a standard, such as ICD-9, ICD-10, CPT, SNOMED, LOINC, COSTAR, and RxNorm coding systems.

Such health care information can be de-identified data such that any personally identifying information is removed, in which case the health care information for a patient is associated with a unique code representing that patient, which code distinguishes the patient from other patients.

Such health care information generally includes both structured and unstructured data. Structured data generally is data that has a specified data model or other organization, whereas unstructured data generally does not. By way of example, structured data can include database records, attribute-value pairs, and the like, whereas unstructured data can be either textual data, such as free text, documents, reports of results, published and unpublished literature, and the like, or non-textual data, such as image data of which DICOM data is an example.

Health care information also can include cost information related to resources for various activities related to providing health care for a patient. Thus, for each activity performed with respect to a patient, resource utilization information also can be made available. Resources can include personnel, equipment, supplies, space, and the like. Resources generally have an associated cost, typically represented by a cost per unit, cost per unit of time, cost per unit of space, and the like.

The data storage 102 that stores such health care information can include a database, such as a relational, object-oriented, or other structured database, such as a structured data file that stores data in columns, optionally in key-value pairs. The database can be stored on a computer, such as described below in FIG. 6, that is configured to allow access to the health care information by other computers through defined transactions. The computer also can be programmed to perform database operations on the database as part of such transactions. Such a computer supporting the database is configured with sufficient processors, memory and storage to support storage of data in, and access to that data from, data storage 102.

The data storage 102 can include data from multiple storage systems (not shown) for each of multiple entities. While data from multiple entities can remain stored in their respective storage systems, such data can be consolidated in data storage 102. Multiple storage systems of multiple entities typically are distributed geographically, so such consolidation generally occurs by periodic requests for transmission of data over one or more computer networks (not shown) to the data storage 102.

The computer system includes a plurality of classifiers 104 (104-1 to 104-N, hereinafter individually or collectively "104"). Classifiers generally are implemented on one or more general purpose computers, such as described below in connection with FIG. 6, programmed by one or more computer programs to implement a classification process.

The classifiers 104 process patient data 106 from the health care information data storage 102 related to patients to determine a likelihood that a patient belongs in a category. A classifier 104 is defined for each category, thus providing N different classifiers for N different categories. A category is associated with a medical condition or procedure for which outcome scores are to be measured and tracked.

The health care information system can include a training process that implements machine learning techniques to train the classifiers 104 given training data 108, including data for a set of patients. In some implementations, trained classifiers can be used. In some implementations, and for some categories, a classifier can be a simple rule applied to the patient data. For example, whether a patient has received a specific surgical procedure can be determined without a trained classifier. After training, a trained classifier 104 applied to patient data 106 for a patient determines a likelihood that the patient has a condition corresponding to the classifier, indicated as categorization data 110 in FIG. 1. For each classifier, the health care information data storage 102 can store categorization data 110 over time for each patient, indicating whether the patient is likely in the category represented by the classifier.

A classifier 104 can be built using any of family of algorithms described as supervised classification or machine learning or econometrics algorithms, which perform functions such as classification, prediction, regression or clustering. With such algorithms, a computer generates a model based on examples provided in a training set. Any supervised classification or machine learning model can be used as a classifier, such as support vector machines, conditional random fields, random forest, logistic regression, decision tree, maximum entropy, artificial neural networks, genetic algorithms, or other classifier or predictive model, or combination of such models, for which parameters of a function can be trained by minimizing errors using a set of training examples. Such models generally produce a score, which can be indicative of a classification or prediction, and a probability. In some cases the score and probability are one and the same value.

Additional data fields 112 can be associated with a category. For example, if the category is associated with a specific health program, then the additional data fields can include any data fields for which data is collected as part of that health program. After a patient is classified in a category, the health care information system adds the data fields for that category to the patient record. These additional data fields can be structured to store a value and a probability indicative of a level of certainty about that value. The health care information system can populate these additional data fields with values and probabilities for those values in a number of ways. For example, the health care information system can derive values for the additional data fields for a patient from existing health care information for the patient, using a data processing module 120 described in more detail below. As another example, a health care information system can prompt users to enter data, such as forms to be completed by patients or their health care providers. The health care information system can be configured to derive values for these fields probabilistically, using one or more classifiers, which in turn provides both a value and a probability associated with that value to be stored in the additional data fields.

The category in which a patient is classified may be associated with a health program, such as a health outcomes measurement program, or a clinical program, or a clinical trial, or a clinical study, or a clinical care program or a treatment program. If the probability that a patient is classified in a category exceeds a threshold, then the health care information system can initiate an automatic enrollment process 130 to enroll the patient in any health program associated with that category. In some instances, the additional data fields 112 added to the patient data are specified by the health program, and the automatic enrollment process adds these data fields to the patient record. The automatic enrollment process also can specify data entry forms to be presented to the patient on a regular basis to provide for further systematic data collection.

The health care information system also includes an outcome function for each category for computing an outcome score for patients in that category. The outcome function for a condition for a patient is a weighted function of one or more scores based on several factors, such as patient and/or caregiver reported outcomes, clinical response measures, survival, events of interest and resource consumption. That is, given a score for each factor for a condition for a patient, based on that patient's data, the health care information system computes a weighted function of one or more scores to compute the outcome score. The set of weights used to compute the outcome score for a condition for a patient is the same across all patients with the same condition. The health care information system can be programmed to allow the set of weights to be changed to allow for analysis of how outcome scores are affected by different weights.

The health care information system includes an outcome calculator 160 that periodically computes an outcome score 162 for each patient, for each condition which the patient has, i.e., for each category in which that patient is classified, using the patient data 164. At any given time point in an historical patient record, the health care information system can compute an outcome score for the condition for the patient. The health care information system can compute the outcome score for a condition for a patient at many points in time, over time. A patient can have multiple conditions for which the health care information system separately computes separate outcome scores 162.

The computer system can include a data processing module 120 that performs various processing on the patient data 106 stored in the data storage 102, so as to convert patient data into additional data and features 122. Such additional data and features can be used, for example, by the classifiers 104, or other components of the computer system. The data processing module 120 also can be implemented using a general purpose computer such as described in FIG. 6 and programmed to perform such processing.

For example, the data processing module can populate the additional data fields 112 for a category, or any other data field missing a value, with values, and optionally probabilities for those values, in a number of ways. For example, the health care information system can derive values for the additional data fields for a patient from existing health care information for the patient. A function can be associated with the data field to define how to derive the value for the data field as a function of other patient data. As another example, the data processing module can prompt a user to enter data, such as by presenting a form to be completed by a patient or a health care provider. The data processing module can derive values for these fields probabilistically, using one or more classifiers, which in turn provides both a value and a probability associated with that value to be stored in the data fields. The data processing module can identify similar patients, and generate a value for a data field based on values stored for similar patients.

The data processing module can apply natural language processing techniques to patient data to generate additional features, such as for training classifiers. The data processing module can perform various normalization or filtering operations to ensure data is consistent across records and with a patient record.

The data processing module also can process patient data using a variety of techniques, such as deep learning models, to identify pertinent features in the patient data. In such an implementation, the patient data is represented as a temporal matrix in which one axis is time and another axis is fields of patient data. The fields can be all of the patient data fields, or selected patient fields. This temporal matrix is processed to identify temporal patterns found across patients within a data field or across combinations of data fields. Such temporal patterns can be identified using a variety of techniques, such as image processing, image pattern recognition, matrix convolution, neural networks. The results of such processing can be used to define features for training and applying classifiers, whether for categorizing patients and/or for calculating risk factors. The identified features can be added as data fields in the patient data.

In some implementations, the data in a field can be represented in the temporal matrix as a transition in state occurring at a point in time. For example, a patient may have a diagnosis of diabetes. While a diagnostic code may arise in the patient data record at a point in time, this characteristic of the patient for the purposes of creating the temporal matrix for deep learning analysis can be represented as a first state (non-diabetic), which transitions to a second state (diabetic) at the point in time corresponding to the diagnosis.

Other techniques of extracting features from a temporal matrix constructed from patient data can be used. For example, an approach as described in "Risk Prediction with Electronic Health Records: A Deep Learning Approach", by Cheng, Y., Wang, F., Zhang, P., Hu, J., in *SIAM International Conference on Data Mining (SDM)*, 2016. can be used.

A particular kind of data processing useful to analyzing health care outcomes for patients is the determination of risk factors for those patients, such as a risk of readmission to a hospital, risk of complications due to surgery and the like. The health care information system also can include risk calculators 170 that compute such risk factors 172 in view of patient data 174.

Risk calculators 170 also can be built using any of family of algorithms described as supervised classification or machine learning or econometrics algorithms, which perform functions such as classification, prediction, regression or clustering. With such algorithms, a computer generates a model based on examples provided in a training set. Any supervised classification or machine learning model can be used as a classifier, such as support vector machines, conditional random fields, random forest, logistic regression, decision tree, maximum entropy, artificial neural networks, genetic algorithms, or other classifier or predictive model, or combination of such models, for which parameters of a function can be trained by minimizing errors using a set of training examples. Such models generally produce a score, which can be indicative of a classification or prediction, and a probability. In some cases, the score and the probability are one and the same value. For a risk calculator, this score and/or probability may be associated to the risk or likelihood of a future outcome or to the likelihood that the patient belongs to a certain cohort by disease type or disease severity.

A risk calculator can be associated with a category into which patients are classified. Thus, a risk factor associated with a category can be calculated for each patient classified in that category. The calculated risk factors can be stored as additional data fields for that category, and can include probabilities related to the risk factors.

The health care information data storage 102 can include a server computer (not shown) implemented using a general purpose computer such as described below in connection with FIG. 6 to control the execution of operations by the classifiers 104, auto enrollment 130, data processing module 120, outcome calculator(s) 160 and risk calculator(s) 170. Each of these components can have its own application programming interface (API) implementing a service oriented architecture. An API can be implemented that provides security, such as via SSL/TLS encryption with user authentication. Programs execution by the health care information data storage 102 can schedule and control processing performed by the other components. Patient data 106 can be processed by such components periodically in batch jobs, such as daily or weekly or other periodic execution.

The health care information data storage 102 also can be accessed through one or more server computers 150 over a computer network 152 through an application programming interface. While only one server computer 106 is shown in FIG. 1, configurations of multiple server computers also can be used. In the example shown in FIG. 1, a plurality of client computers 154-1, . . . , 154-M, (hereinafter "154") communicate with one or more server computers 150 by connecting to a computer network 156 and transmitting messages to, and receiving messages from, the server computer 150 using a communication protocol over the computer network 156.

The one or more server computers 150 can be implemented using a general purpose computer such as described below in connection with FIG. 6. The general purpose computer is configured as a server computer, with sufficient processors, memory, storage and communication connections. In one example implementation, the server computer can be configured to operate as a "Web" server, or a server computer that implements a hypertext transfer protocol (HTTP) or secure hypertext transfer protocol (HTTPS), using a computer program such as the Apache web server computer program or other similar web server computer programs. Using an HTTPS server implementation, users can login with secure connections and have permissions associated with their user sessions which in turn can be used by the one or more server computers 150 to provide a personalized user experience for each user and to ensure each user accesses only those data records in storage 102 for which the user has authorization. For example, a patient is limited to accessing that patient's own records. A health care provider is limited to accessing only patient data for its patients. Access control by roles within a health care provider, for example a doctor may have access to more patient data than someone in an administrative role, also may be provided.

The computer networks can be any type of computer network that allows computers to communicate messages with each other. An example computer network is an Ethernet network, which supports local and wide area networks, and which can support communications using an internet protocol (IP). The computer network can be public (such as the internet) or private (such as a private network supporting IP). Multiple types of networks may be involved in connecting the one or more client computers 154 to the one or more server computers 150.

The client computers 154 can be any kind of computer, generally in the form of a general purpose computer such as described below in connection with FIG. 6. For example, the client computer can be a desktop computer, laptop or notebook computer, or mobile computing device such as a smartphone, tablet computer, handheld computer and the like.

In one example implementation, a client computer 154 is configured with a computer program called a "web" browser application which implements both communication protocols and rendering conventions for exchanging information with "web" server computers. Such a browser application generally allows the client computer to communicate with a server computer over a computer network using HTTP, HTTPS or similar communication protocol, and renders and displays documents received in a markup language or other standardized format supported by the browser application. Example browser applications include, but are not limited to, the Firefox, Chrome, Safari, Internet Explorer browser applications. In another example implementation, a client computer can be configured with a dedicated computer program, or application, that is designed to interact primarily with the one or more server computers 150.

Through a client computer 154, various operations with respect to the health care information stored in data storage 102 can be provided by the server computer 150 to end users.

For example, a client computer 154 can present a graphical user interface that presents, for each patient, the outcome score for a selected condition for the patient, whether at a current point in time, a past point in time or over a period of time. The graphical user interface can present information about how the outcome score is computed, based on the weighting function and the underlying scores for the different factors.

Also, a client computer 154 can present a graphical user interface that presents forms for data entry, through which a user can enter data requested to populate the additional data fields for a patient based on the categories in which the patient has been classified. Such data entry forms can be presented to various users, such as care providers and patients, to provide, at least in part, the patient reported outcomes and clinical response measures used in computing outcome scores for patients.

Turning now to FIG. 7, an illustrative example implementation of data structures stored in the health care information storage 102 will now be described. The example in FIG. 7 illustrates data for patient records pertinent to tracking and determining their health care outcomes as described herein. Other data sets, such as those providing demographic information, insurance information, provider information, and relationships among patient and providers, can be stored in other database structures using conventional techniques.

In FIG. 7, a patient record 700 has a patient identifier 701 and includes a number of base fields (702-1 to 702-X). These base fields can be structured, such as by having a key 704 and value 706, or unstructured, such as by having a name 708 and unstructured text field 710. Some of the structured data fields can be created by processing unstructured data; some missing data in structured data fields can be imputed by processing data from other fields, and similar data from similar patients. There can be a very large number of base fields 702.

The patient record 700 also can have a number of category fields 712-1 to 712-N which represent categories into which a patient can be classified. A category field can have an identifier 714 identifying the category and a value 716 indicating a likelihood that the patient is classified in that category. Other data 718 can be stored for the category, such as a name of a health program or condition associated with the category, model type and/or model name or other information about the classifier used to match the patient to this classifier and/or statistics obtained from applying that classifier to the patient. The other data 718 also can include information for tracking any schedule of patient data entry for patient record outcomes based on this category.

Next, if a patient is classified in a category, any additional data fields 720-1 to 720-Y for that category are added to the patient record. These additional data fields can be structured or unstructured data fields. For example, an additional data field can be in the form of a key 722, value 724 and probability 726 indicating a likelihood that the stored value 724 is correct. An additional data field may represent a risk factor to be computed for patients in that category. As another example, the additional data field can refer to or include image data. If an additional data field is specified by different categories, then that additional data field can be added only once to avoid redundancy. Some data for an attribute can be stored as a time series, such as for values that are regularly reported as part of patient reported outcomes. For example, a date/time 728 can be stored for different instances of the attribute in the time series. The patient data can be logically organized in the data storage in part by condition, and attributes stored for patients can be organized in a nested structured in part by condition.

For storing outcome measures, for each category in which a patient is classified, outcome scores over time are stored. Thus, outcome data 730-1 to 730-N includes a category identifier 732, a time 734 and factor scores 736-740 for each factor for which a score is computed. The example shown in FIG. 7 shows five such factor scores. The outcome value 746, computed as a weighted combination of the factor scores, also can be stored. Examples of other data that can be stored is an indication of the method used to compute the outcome score from the factor scores.

It should be understood that the foregoing description of data representations is illustrative. In some implementations, there may be multiple data storage systems that store data in different formats for different purposes. For example, one database, herein called a standard database, can store such data in a format that is optimized for updating. Another database, herein called the analysis database, can store such data in a format that is optimized for performing queries and analytics on the data, such as a structured data file which stores data in columns in the file and is stored in a distributed file system. Another database, herein called a transaction database, can be used for managing data transactions in real time that input data. Periodically data can be transferred from the transaction database to update the standard database, and the updated standard database can be processed to update the analysis database.

The standard database also can be associated with a variety of data processing modules that extract, transform and load data from various sources, such as various electronic health and medical record systems from a variety of sources, into the standard database. Such processing can include linking data for a patient from different sources, deduplicating data records and normalizing data records across sources. In some implementations, separate databases, or separate access controls on data, can be provided to segregate data that is de-identified from data that identifies patients, providers and/or other entities.

Multiple instances of time data can be associated with a data field. Time can be stored for when an event occurred, when data was received, and when data was generated (such as a report or a value generated by the system to populate and incomplete data field).

Figure 2:
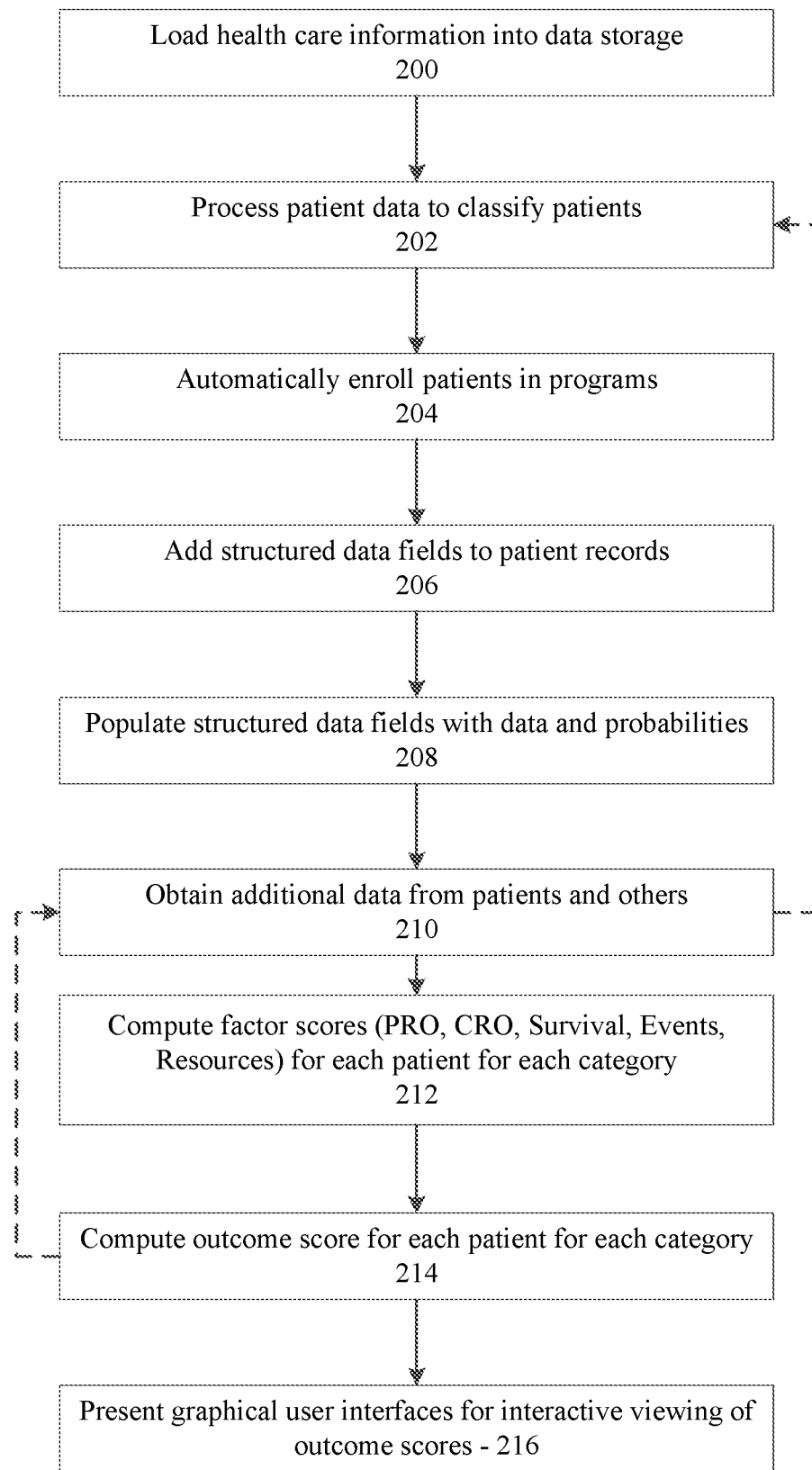
FIG. 2 is a flow chart describing an example implementation of operation of the computer system of FIG. 1.

Turning now to FIG. 2, a flowchart describing operation of a computer system such as shown in FIG. 1 will now be described. While this flowchart and corresponding description presents this operation as a single sequence of steps, these steps can be performed at different points in time, and in a different order. For example, information about patients can be loaded into the system and/or updated at any time. Processing of patient data to categorize patients, add and update data fields, and update scores can be performed as daily batch jobs on the databases. Interaction by end users with the database can occur at any time.

Health care information for multiple patients, such as described above, is loaded 200 into the data storage. The patient data is processed 202 to classify patients into categories. In particular, for each available category, a probability is computed and stored for each patient. When such processing is done periodically, the probability of an association of a patient to a category can be viewed over time. Patients then optionally can be automatically enrolled 204 in any health program associated with the category in which the patient is classified.

Any additional data fields related to the category in which a patient is classified are added 206 to the patient record. These additional data fields are populated 208, in part by automatically processing the existing patient data. Such automatic processing can result in a probability that the underlying data supports having a particular value stored in one of the added data fields, and this probability also can be stored.

Over time, additional data can be obtained 210, from patients, caregivers and other sources, for structured data fields based on data entry forms for patient reported outcomes, clinical response measures, events of interest, survival and resource utilization. As noted by the dashed line from 210 to 202, the health care information system periodically processes the current patient data as updated over time through steps 202-210.

Periodically, a set of factor scores is computed 212 for each patient, for each category in which the patient is classified. An outcome score is computed 214 for each patient for each category in which the patient is classified, using an outcome function defined for that category, as a weighted function of the factor scores.

Given computed factor scores and outcome scores, various graphical user interfaces can be presented 216 to a user to allow interactive viewing of such information, such as outcome scores and risk factors, for one or more patients.

More details of example implementations of the steps in FIG. 2 will now be described in connection with FIGS. 3 through 5.

Figure 3:
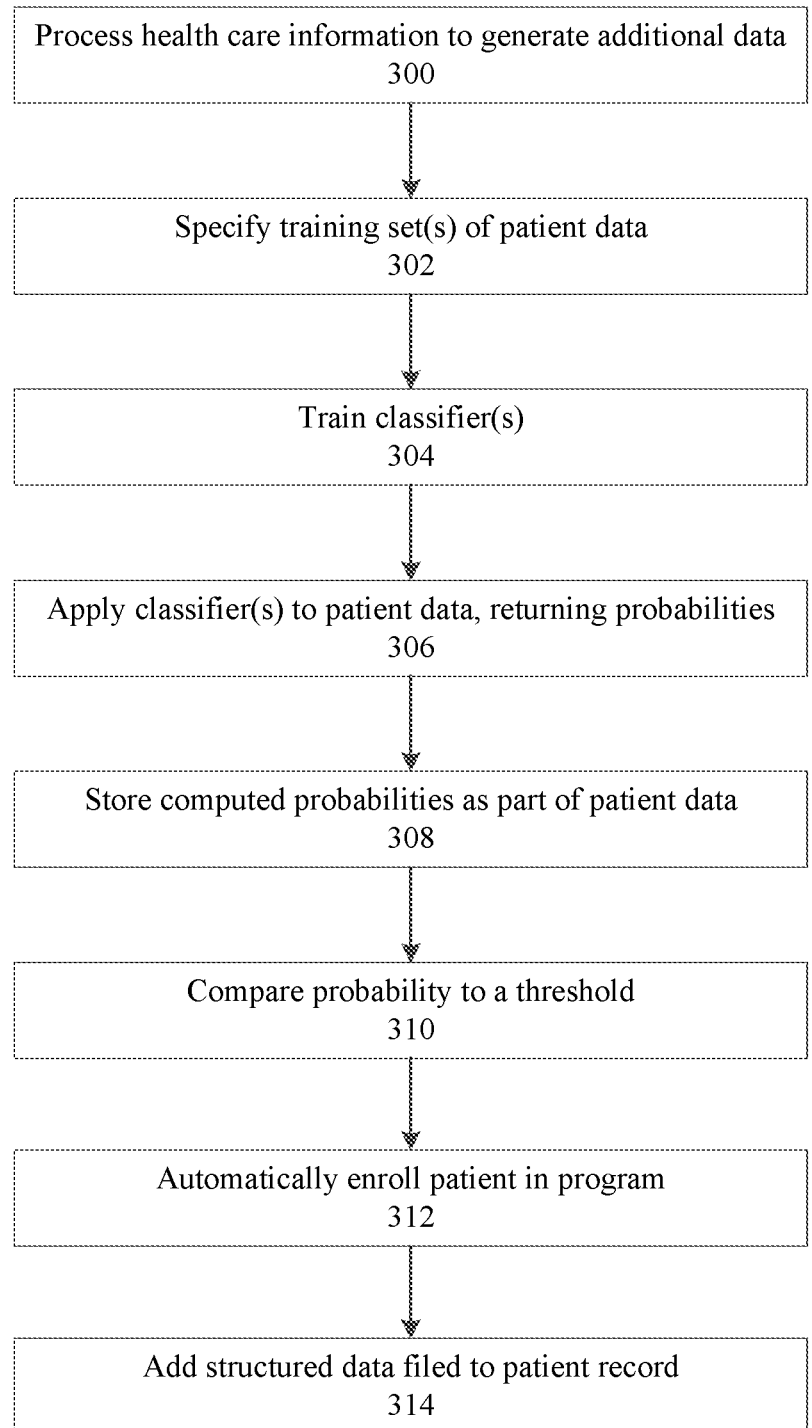
FIG. 3 is a flow chart describing an example implementation of classification of a patient in a category.
Figure 4:
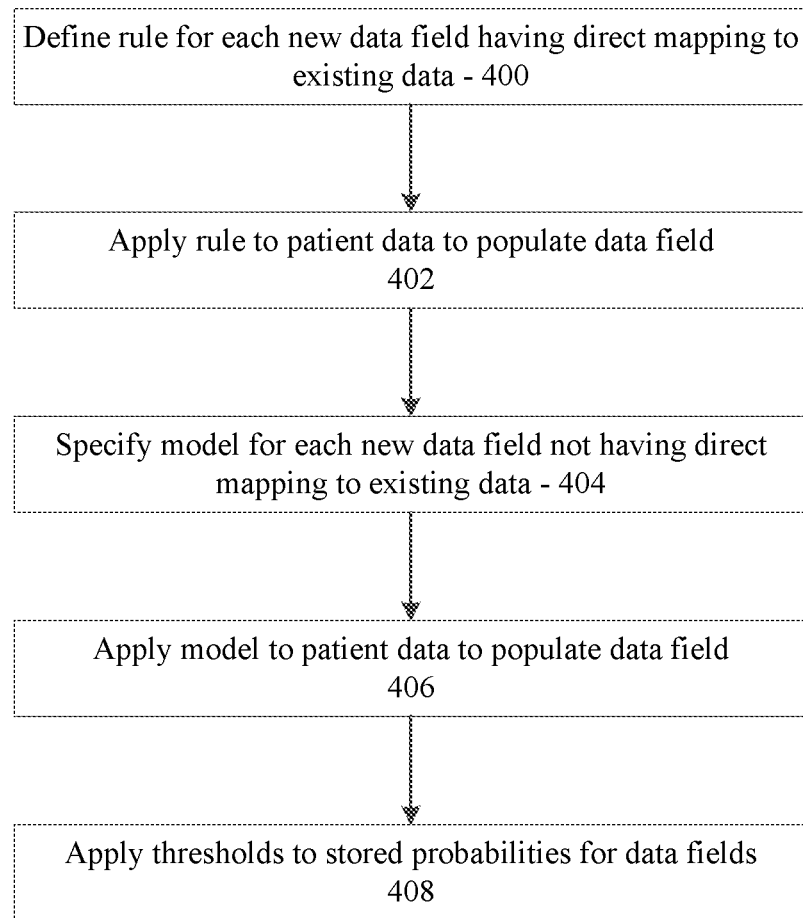
FIG. 4 is a flow chart describing an example implementation of populating data fields with missing values.

Turning now to FIG. 3, a flowchart describing one example implementation for classifying patients into categories.

The health care information in the data storage can be processed 300 to generate additional data, which also can be stored in the data storage. For example, natural language processing can be applied to textual, unstructured data to generate such additional features which in turn are stored in the patient data. For example, natural language processing can extract key words and data types, and apply patterns, defined based on the targeted features, to such key words and data types to detect values for the features. As another example, "deep learning" algorithms can be applied to the patient data to identify features and values for those features. All of the fields of data available for a patient can be considered features from the perspective of training a classifier and classifying patients with a trained classifier.

A training set of patient data is specified 302 for each category for which a classifier is to be built. The training set includes data for patients that are identified as representative of a particular category, i.e., true positives, and can also use data for patients that are identified as non-representative, i.e., true negatives. The category can be defined, for example, as patients that meet criteria for participation in a health program, such as a health outcomes measurement program, or other clinical program or clinical trial or clinical study. The training set can be manually selected by experts, for example. The training set can be automatically selected given criteria that can be applied through queries of the health care information, such as all patients having a particular diagnosis code in their medical records. Given a set of training data for a category, a classifier is trained 304 using conventional machine learning techniques. Training of classifiers to determine risks for patients can be generated in a similar manner using a training set of patient data from the database 102, or another database, or by accessing a trained classifier, and then applying the trained classifier to patients data from the database 102.

After one or more classifiers are trained, the trained classifiers are applied 306 to the health care information stored for patients. For each patient, each classifier returns a probability that the patient meets criteria for a particular category. A classifier also can return other values and probabilities associated with those values, such as a likelihood of improving with a particular treatment and a likelihood of experiencing a future event or outcome. If such values exceed a threshold, a notification can be generated and transmitted to a health care provider, or a patient or other individual. The probabilities computed by each classifier for a patient are stored 308 for the patient.

The probability computed for a category can be compared 310 to a threshold for the category to determine whether the patient is associated with that category. The threshold may correspond to qualifying to participate in a health program. If the probability exceeds the threshold for a health program, then the patient can be automatically enrolled 312 in the corresponding health program, which can include adding the patient to a list of enrolled patients for the health program, sending the patient information through a form of electronic communication, such as electronic mail or text messaging. Provisions can be made for a patient to opt out of a health program.

After a patient is associated with a category, additional data fields associated with that category can be added 314 to the patient record for that patient. Such additional data fields can include, for example, targeted data structures based on a case report form for a clinical trial and or registry. Such targeted data structures can be programmed into the system to correspond to, for example, a case report or other set of data that is useful to collect from patients classified in a category. These additional data fields for a category are designed to capture information useful in computing outcomes scores for patients classified in that category.

Given the additional data fields, a process for populating such data fields, and other data fields missing values, with values will now be described in connection with FIG. 4.

A rule can be defined 400 for each new data field for which data in the existing health care information has a direct correspondence. Thus, a rule generally provides a value for a new data field as a function of other existing data fields in a patient's record. Such rules can be predefined for each additional data field to be added for a category. Such a rule also can be defined generically for all patients to provide a value for a data field that otherwise is missing a value. Such rules are executed 402 for each patient that is added to a category to populate the additional data fields for the patient based on the existing data, or for all newly added patients, or for newly added rules.

For some of the additional data fields that are added to a patient record of a patient who has been assigned to a category, there is no direct correspondence with the existing data, or some of the existing data may be incomplete or inaccurate. For such a data field, a model can be specified 404 that predicts a likelihood that the data field is supported by the data in the existing health care information. That likelihood may be represented by a probability, a derived statistic, a rank order or some other means to show the relative likelihood that the data field can be completed using the existing health care information in the system. The model is then applied 406 to the data to generate a likelihood value to be stored for that data field.

Such models can be developed by training a classifier for the data field. In one implementation, experts review a sample of medical records and other data sources and complete the targeted data structures using expert knowledge. In other implementations, rules may be created which look for data in the source data fields to create the sample data set. This sample comprises the training set. This selection of a training set is repeated for each data field which can be completed, such as each of multiple targeted data structures constituting a case report form for a health program. Second, the training data is used to train a series of models to use available data from each medical record to generate values for the data fields with missing values. Such models can generate a probability that the underlying data for a patient record supports a particular value in the data field being populated. Such data fields can represent such information as "Is the patient a current smoker", with a value of Yes or No and a probability, or "What is the level of renal failure", with possible values of Mild, moderate, Severe, and a probability. Such data processing also can be applied to complete the base fields of a patient record that are incomplete. Such data processing also can be applied to identify risk factors for a patient.

A threshold probability can be set for, and applied 408 to, any data field for which a model is used to compute a value and a corresponding probability. When the threshold probability is surpassed by a computed probability related to a computed value for that data field, the value of that data field can be set to the computed value. In one implementation, if the threshold probability is not exceeded by the computed probability from the model, the value for the data field is not set. In other implementations, the value of the data field can be set to a computed value having a highest computed probability. In some implementations, for some data fields, the computed value and the computed probability are the same value which can be stored as the value for the data field. For example, if the stored probability is 0.95, then a calculation using this data field can conditionally use a value based on the stored probability. In such an implementation, the probability can be stored in place of the value for the data field; thus a separate value for the data field can be omitted from the stored data.

Figure 5:
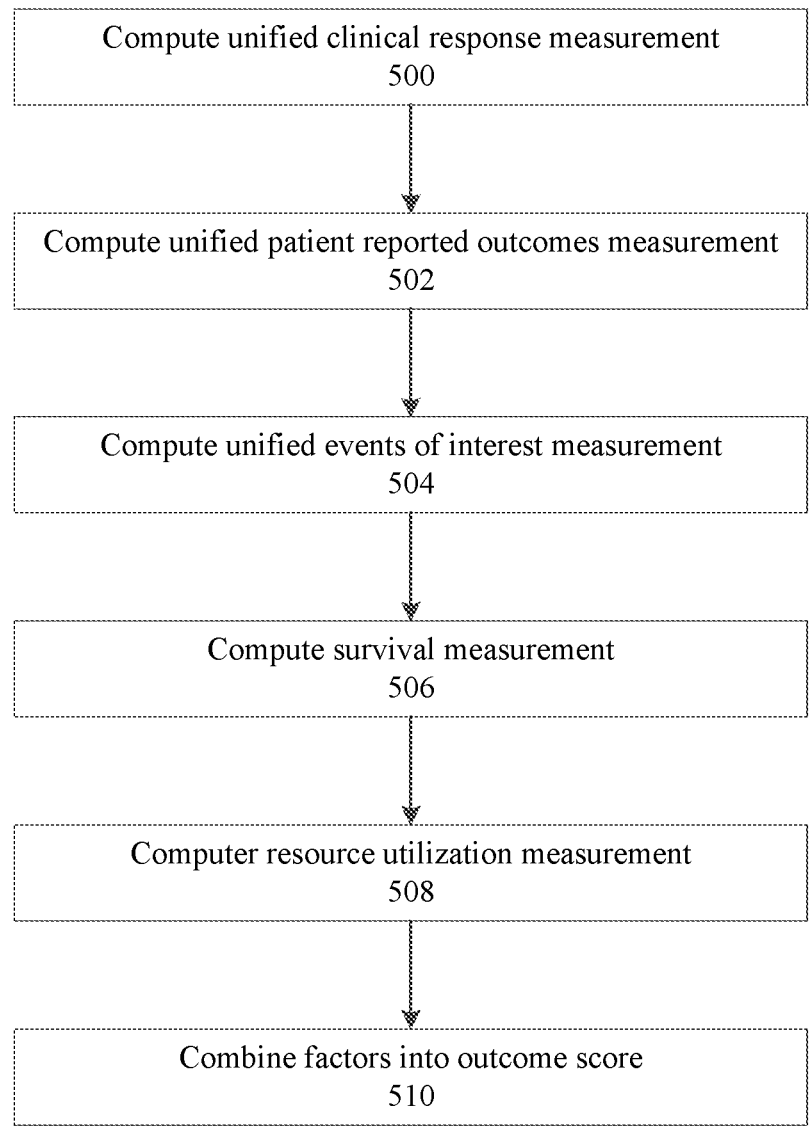
FIG. 5 is a flow chart describing an example implementation of computing outcome scores.

Turning now to FIG. 5, an example implementation of an outcome calculator 160 in FIG. 1, describing how outcome scores can be computed for each patient, for each category in which the patient is classified, will now be described in more detail.

The outcome score so computed uses one or more factor scores that: 1) are specific to a condition; 2) are specific to a time point relative to an episode of care or treatment or at a fixed time interval from baseline or a regular repeated measurement points such as annually; 3) utilize a standardized reporting framework; and 4) create a unified condition specific health score. The unified condition specific health score, also called the outcome score herein, is calculated from at least one of five factor scores based on an algorithm that separately weights each underlying factor score, and combines the weighted factor scores into a single value. The algorithm can vary, for example, by condition, by time point and by user group or by other categorization of the data. By determining a unified condition specific health score at each time point, patient outcome scores can be directly compared from one time point to another, allowing a more standard metric for reporting of outcome scores for each condition.

This standardized framework for generating an outcome score for a condition can be used for each health condition where a patient's factor scores can be computed for a particular point of time, and can use, in this example, up to five factor scores that are related to healthcare outcomes. Those factor scores are patient reported outcomes, clinical response, survival, events of interest and resource utilization.

Survival signifies a patient surviving or not surviving up to that time point. The survival factor is further based on whether death occurs as a result of the condition being reported or not.

Clinical response signifies metrics defined by clinicians regarding how they perceive the patient is doing. These differ by condition. For example, with cancer, clinical response metrics can include progression of disease (growth of tumor, spread of tumor) or regression of disease (reduction in tumor) or control (no progression or regression). Such metrics can be represented as numbers of episodes or exacerbations (e.g. frequency of headaches in a headache patient or number of exacerbations in an asthmatic patient). Such metrics can be represented by a clinical laboratory value or other clinical assessment value or values, e.g., a hemoglobin a1c level in a diabetic, or a viral load in an AIDS patient, or liver function in a cirrhosis patient, or glomerular filtration rate in a kidney disease patient, or clinical rating scale in a rheumatology patient.

Events of interest refers to specifically defined events or encounters that can be predefined by clinicians as demonstrating some unexpected but negative event. Examples of events of interest include, but are not limited to, a surgical complication, such as severing a nerve; an adverse event to a medication, such as an allergic reaction; a readmission to a hospital or visit to an emergency room; a wound infection after surgery; a pneumonia after a general anesthetic; a stroke immediately following a trans-vessel procedure such as a percutaneous angioplasty; or a second heart attack after a first heart attack. Events of interest may be represented as a history of events, and a pattern of events within this history can be relevant to a score.

Patient-reported outcomes are outcomes that are relevant to a patient or caregiver, such as health related quality of life or the ability to perform activities of daily living. There are numerous quality of life measures across many different healthcare conditions. These measures often have different scoring methods and scales going from high to low or low to high. Examples include Likert scale based validated questionnaires and 1-10 or 1-100 mm scales such as visual analogue scales.

Measures that reflect the consumption of resources can include resources noted specifically in cost or as itemized consumption of supplies or personnel hours, or more generally as hospitalizations, treatments, emergency room visits, home care visits, pharmaceuticals and so forth. They can also include non-healthcare costs such as loss of time from work, reduced productivity at work and so forth.

For each condition, at each time point, one or more of these condition-specific factors scores are computed, and then weighted and combined to compute an outcome score. As shown in FIG. 5, the outcome calculator computes one or more of a unified clinical response measurement (500), a unified patient reported outcome measurement (502), and/or a unified events of interest measurement (504) as factor scores. Patient survival may also be reported (to computer a survival measurement 506) at each time point when the information is available. However, if a patient has not survived to the specific time point, then the unified clinical response measurement and the unified patient reported outcome measurement are not measurable for that time point. Resource utilization may also be computed (508) for any interval up through the time point being reported. The outcome calculator then combines (510) one or more of these factor scores to produce the overall outcome score for that patient for that condition.

The computation of outcome scores at multiple time points enables both current status of the outcome score and change in the outcome score over time to be easily reported in simple graphics. This standardized computation of outcome score for multiple patients further enables different user groups to provide different weights to the factor scores that are included in the measurement at any specified point in time relative to a baseline. It also may allow different weights to be provided by panels for the measurements comprising the factor scores as well. For example, a particular group may seek a patient panel to provide input on how to weight the five factor scores for evaluating condition specific outcomes for the one year point. Such a group might also provide input on whether to weight a visual analogue scale or a VR-12 scale in the patient reported summary score differently or equally. The value of this flexibility is that different end users may find that different weightings provide more information to their particular stakeholder group or for particular decision making.

An outcome score based on one or more of the patient reported outcome measurement, clinical response measurement and events of interest measurement can be reported on a numeric scale, such as numeric values or percentages, such as a scale of 0 to 1000, 0 to 100, 0 to 10, 0 to 1, or an arbitrary scale. The unified condition specific health score that may be further modified by a survival score. The unified condition specific health score that may be further modified by a resource utilization score.

The outcome score can be a weighted combination of one or more of these factors. The relative weights can be changed for specific conditions and for specific timepoints of the unified clinical response measurement, the unified patient reported outcome measurement, the unified events of interest measurement, the survival score and the resource score.

In one example, the unified condition specific clinical response measurement can be computed (500) by converting n condition-specific clinical response measurements to n scales normalized on a similar scale for combining otherwise disparate measurements [Constant 1×clinical status measurement A (normalized to common scale)+Constant 2×clinical response measurement B (normalized to a common scale)+ . . . +Constant n×clinical response measurement n (normalized to common scale)] divided by (Constant 1+Constant 2+ . . . +Constant N). This measurement can be converted to a scale of 0-100 where 0 is the worst possible score and 100 is the best possible score.

In one example, the unified condition specific patient reported outcome measurement can be computed (502) by converting n condition-specific patient reported outcome measurements to n scales normalized on a similar scale for combining otherwise disparate measurements [Constant 1×patient reported outcome measurement A (normalized to common scale)+Constant 2×patient reported outcome measurement B (normalized to a common scale)+ . . . +Constant n×patient reported outcome measurement n (normalized to common scale)] divided by (Constant 1+Constant 2+ . . . +Constant N). This measurement can be converted to a scale of 0-100 where 0 is the worst possible score and 100 is the best possible score.

In one example, the unified condition specific events of interest measurement can be computed (504) as an algebraic sum or a weighted sum of each of the specific events of interest. Each of the events of interest can be individually graded for severity using a numerical grading scale with one or more defined clinical criteria. This measurement can be converted to a scale of 0-100 where 0 is the worst possible score and 100 is the best possible score. Such weighting can be determined based on evidence, literature or through data analysis applied to the patient data.

The unified condition specific health measurement can be computed (510) by combining one or more of a unified condition specific patient reported outcome measurement, a unified condition specific clinical response measurement, a unified condition specific events of interest measurement, a unified condition specific survival measurement, a unified condition specific resource utilization measurement.

In one example, the unified condition specific health measurement can be derived using the following algorithm [Constant 1×clinical response measurement A+Constant 2×patient reported outcome measurement B+Constant 3×Events of interest measurement C+Constant 4×survival measurement D+Constant 5×resource measurement E]/(Constant 1+Constant 2+Constant 3+Constant 4+Constant 5) where Constant 1, 2, 3, 4, 5 may be the same or different and may be any whole or fractional number including 0.

In one example, the unified condition specific health measurement can be derived using the following algorithm [Constant 1×clinical response measurement A+Constant 2×patient reported outcome measurement B+Constant 3×Events of interest measurement C+Constant 4×survival measurement D/(Constant 1+Constant 2+Constant 3+Constant 4) where Constant 1, 2, 3, 4, 5 may be the same or different and may be any whole or fractional number including 0.

In one example, the unified condition specific health measurement can be derived using the following algorithm [Constant 1×clinical response measurement A+Constant 2×patient reported outcome measurement B+Constant 3×Events of interest measurement C]/(Constant 1+Constant 2+Constant 3) where Constant 1, 2, 3 may be the same or different and may be any whole or fractional number including 0.

In one example, the unified condition specific health measurement can be derived using the following algorithm [Constant 1×clinical response measurement A+Constant 2×patient reported outcome measurement B]/(Constant 1+Constant 2) where Constant 1, 2 may be the same or different and may be any whole or fractional number including 0.

The various weights in the foregoing computations can be determined by a statistical analysis of a patient data set with known outcomes. The statistical analysis can determine which fields of patient data contribute most to a specific outcome in a category. Weights can be assigned to such fields of patient data to compute factor scores and outcome scores for the category. In particular, a weight can be assigned to each diagnosis code and procedure code. This weight can be applied to compute the factor score using that diagnosis code or procedure code.

As noted above, given ongoing entry of patient reported outcomes from patients and/or caregivers, entry of clinical response measures and entry of events of interest, and periodic classification of patients, automatic enrollment of patients, and computation of outcome scores, such information can be interactively viewed through a graphical user interface. Such a graphical user interface can allow a patient to, among other things, review medical history. The graphical user interface can allow a health care provider to, among other things, review the patient data for one or more patients, compare data, such as outcomes, among patients, and review risks identified for individual patients.

An example graphical user interface for this example implementation will now be described in connection with FIGS. 8-17.

A graphical user interface generally is implemented as part of an application executed on a computer, and can be implemented using interpretable code executed in a browser application. For example the graphical user interface pages can be built as single-page applications (SPA) using HTML5 including CSS and JavaScript. Each single-page application dynamically loads only the necessary resources (pages, styles, code) for the user's current view and action using asynchronous calls to an application programming interface.

Figure 8:
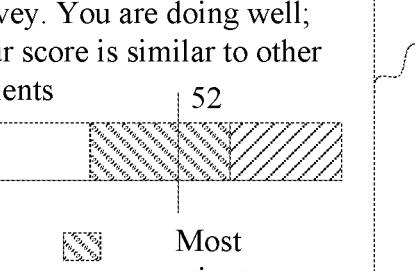
FIG. 8 are example graphical user interfaces for use on a client computer for patient entry of patient reported outcomes.

FIG. 8 are example graphical user interfaces for use on a client computer for patient entry of patient reported outcomes. At 800 an interface prompts a patient to select a value for a structured data field. In this example, the values are limited to a set of five possible selections. At 804, an interface prompts a patient to enter a value for a structured data field. In this example, the values are on a range represented by a sliding scale. At 802, navigation aids are provided. In response to patient input with respect to such aids, the system can transition between different user interfaces for entering different structured data. In response to patient input with respect to one of the options on a given interface, the system stores the value in the patient's data records. Upon completion of the data entry, the system can recompute and display, at 806, a graphical representation of an outcome score for the condition, updated using the recently entered patient reported outcome data.

Figure 9:
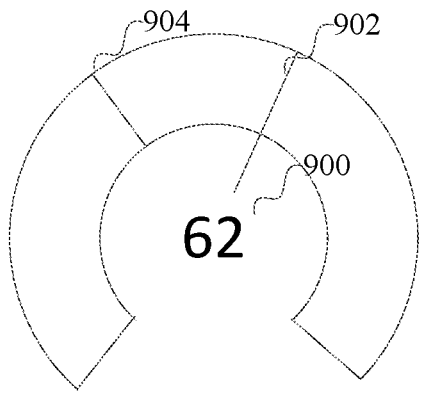
FIG. 9 is an example graphical user interface for use on a client computer to display a graphical representation of a current outcome score to a patient upon completion of data entry for patient reported outcomes.

FIG. 9 is an example graphical user interface for use on a client computer to display a graphical representation of a current outcome score to a patient upon completion of data entry for patient reported outcomes. In this graphical representation, the current score is displayed as a number at 900. The current score also is indicated at a position 902 along an arc representing the range of possible values. A baseline or previous score is indicated at a position 904 along this arc. The appearance of the arc between the positions 902 and 904 can be different from the other sections of the arc, to highlight improvement (such as by making this part of the arc green) or regression (such as by making this part of the arc red).

Figure 10:
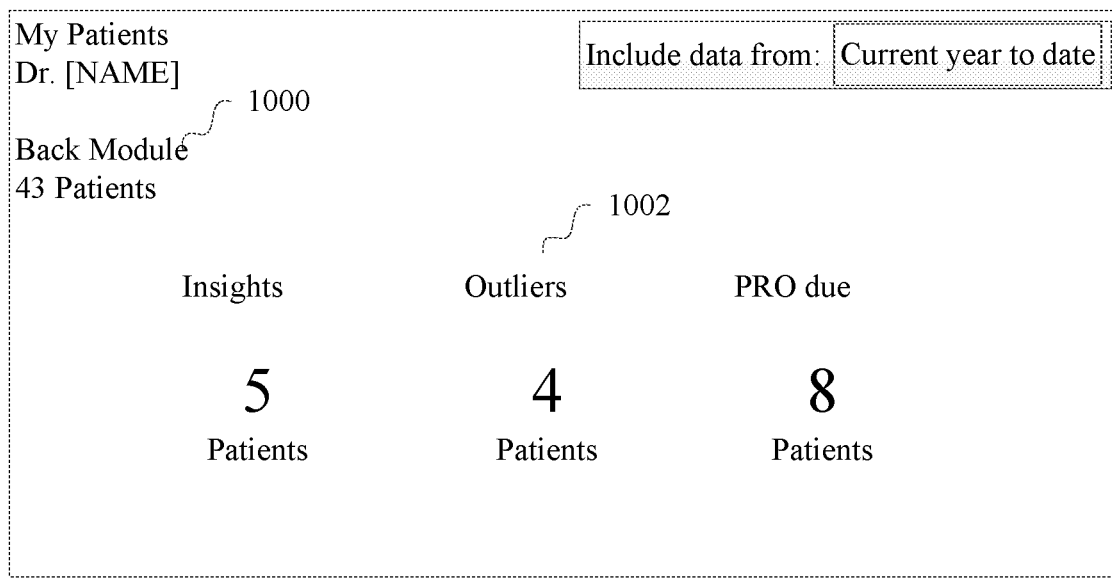
FIG. 10 is an example graphical user interface for use on a client computer to provide a physician's dashboard.

FIG. 10 is an example graphical user interface for use on a client computer to provide a physician's dashboard. This graphical user interface is one example of a navigation-style interface that allows a user to select a subset of patients and then perform analyses and/or view information about patients within that subset. In FIG. 10, the subset of patients is selected by their association with a physician. A variety of different kinds of dashboards can be created for different kinds of users to allow selection of patient subsets and navigation of patients within those subsets.

In FIG. 10, for a given condition, as indicated at 1000, the dashboard can display graphical representation of groups of patients with the condition, such as indicated at 1002. Patients may be grouped by any of a variety of criteria. In this example, patients are grouped by: patients that have "insights" associated with them (such as a classifier, after processing their data, identified a risk of an event occurring); patients that have "outlier" information (such as, after processing their data, some reported data is significantly variant from other patients in the group); and patients that have to input their patient reported outcomes. Such data about the status of these patients can be stored as data fields in the patient data. In response to the physician's input with respect to one of these groups, a more detailed view of the patients in that group can be displayed, such as in FIGS. 11-14. Such groupings can be displayed for each category in which this physician's patients are classified.

Figure 11:
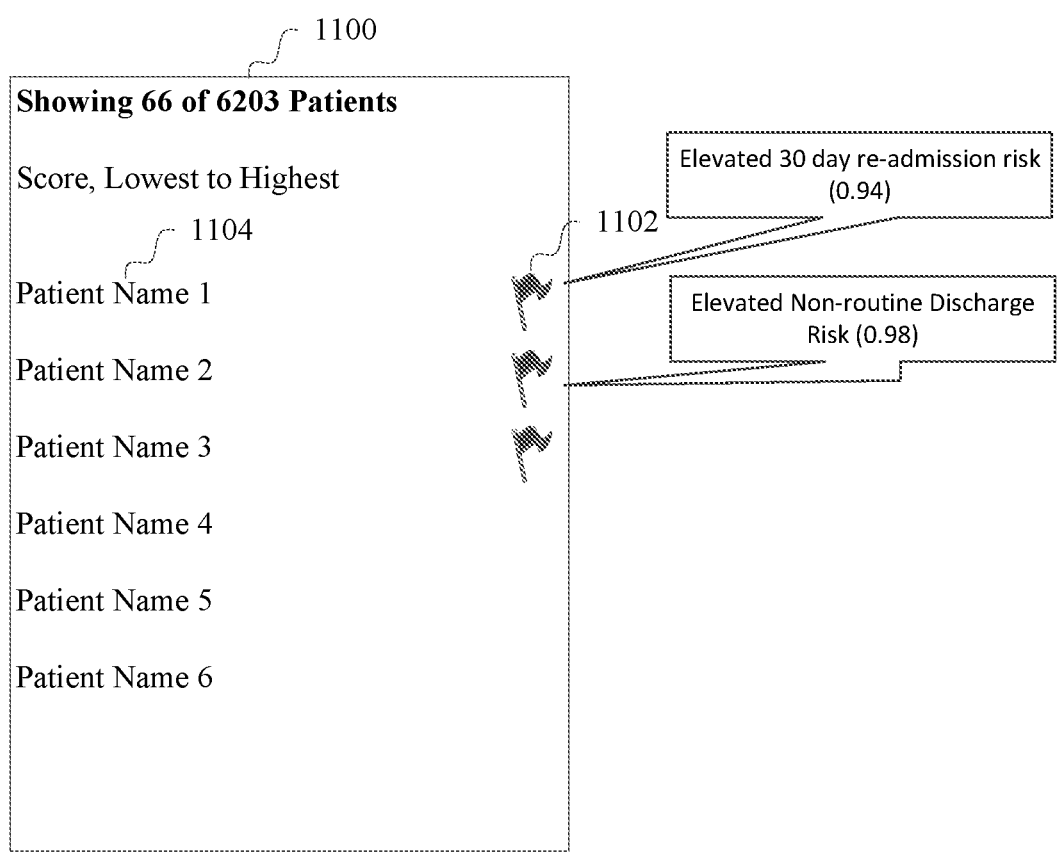
FIG. 11 is an example graphical user interface for use on a client computer to provide a patient list with data indicating patients with detected risks.

FIG. 11 is an example graphical user interface for use on a client computer to provide a patient list with data indicating patients with detected risks. In this example, the system presents a graphical representation of a subset of the physician's patients, such as a list 1100. The subset can be based on, for example, patients in a particular category, i.e., having a particular condition. For each patient having a detected risk flagged in their patient data, an indicator 1102 of that risk can be shown next to an indicator 1104, such as a name, for that patient. The risk indicator can be determined, for example, using a classifier developed for the category of patients which detects patients that may have a risk of an event or condition, using information about patients known to have had that event or condition. The risk indicator for a category may be one of the additional data fields added to a patient record if that patient is classified in that category. Given the displayed list, in response to a physician's input with respect to a displayed representation of a patient, the system can access and display information for that selected patient.

Figure 12:
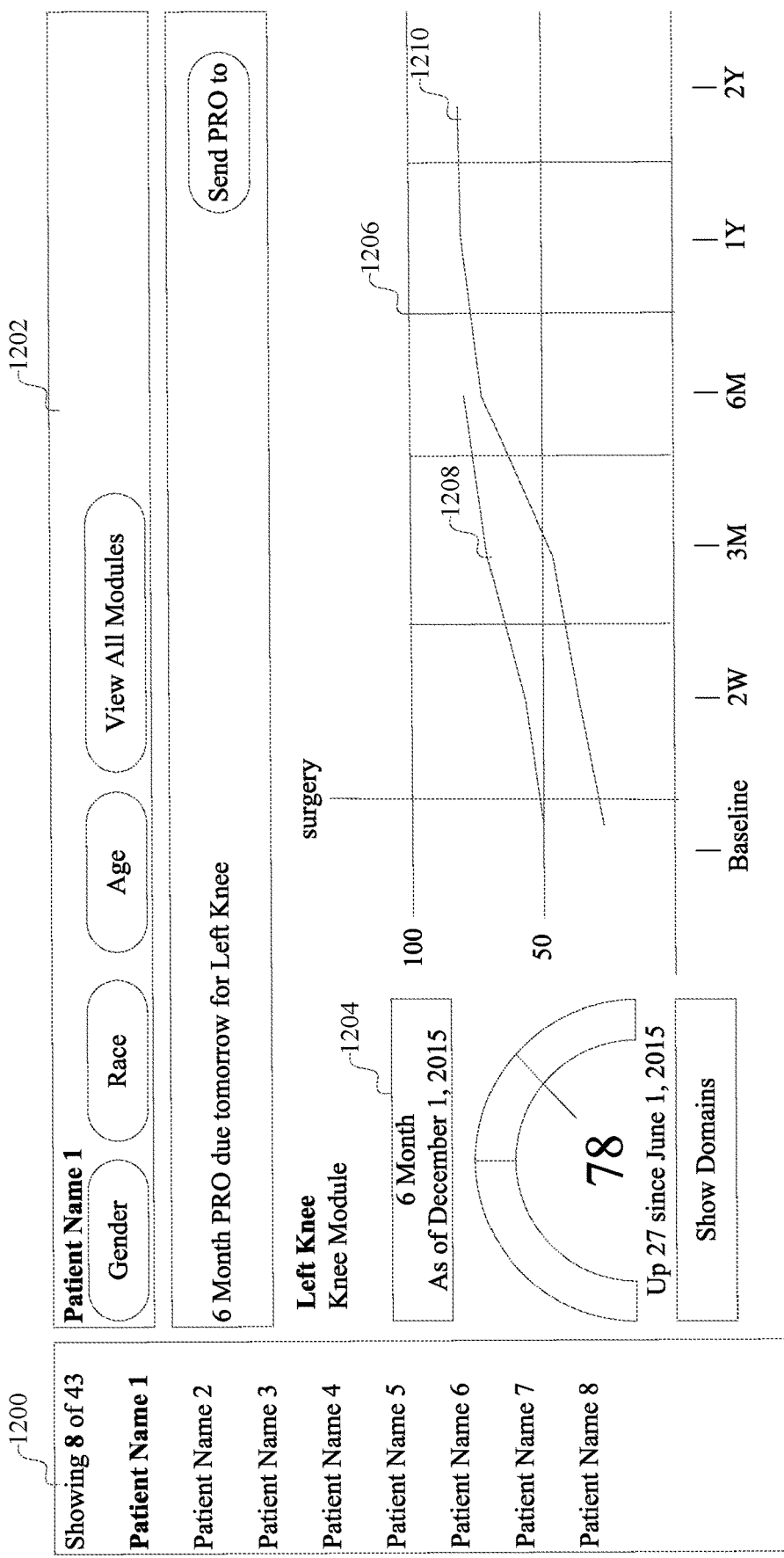
FIG. 12 is an example graphical user interface for use on a client computer for a physician to view data about a patient.

FIG. 12 is an example graphical user interface for use on a client computer for a physician to view data about a selected patient. This interface can include a graphical representation of a patient list 1200. In response to selection of a patient, the information for the selected patient is shown in area 1202 of the display. The displayed information can include a graphical representation of the patient's current outcome score 1204 for the selected condition. This display is similar to the one shown to patients in FIG. 9. A timeline view 1206 of the outcome score over time also can be displayed. The timeline view can show the outcome score of the patient, e.g., at 1208, in comparison to a reference, e.g., at 1210, such as a national average, average of patients of that physician or health care facility, or other reference.

Figure 13:
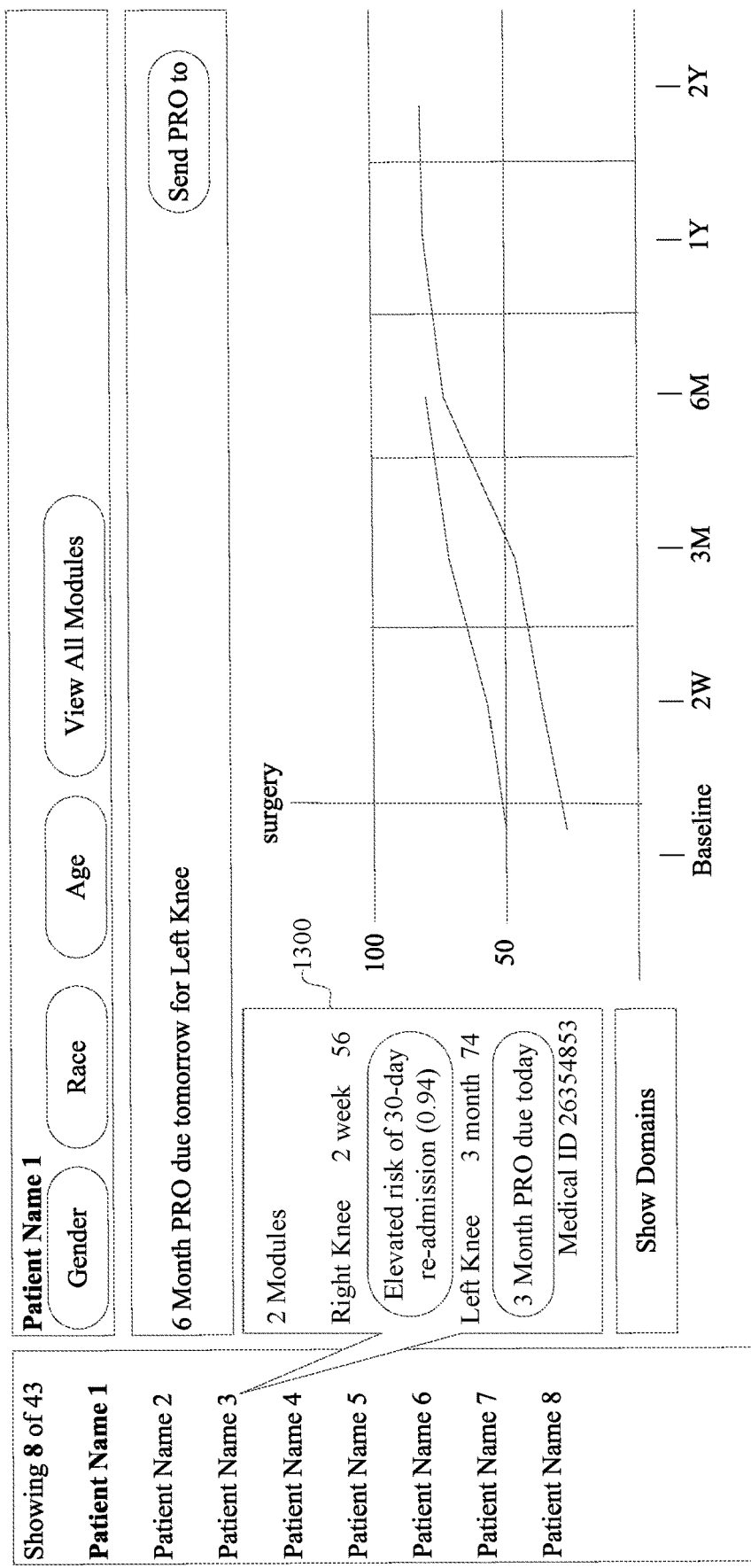
FIG. 13 is an example graphical user interface for use on a client computer showing more detail of use of the interface of FIG. 12.

FIG. 13 is an example graphical user interface for use on a client computer showing more detail of use of the interface of FIG. 12. In FIG. 13 a contextual menu 1300 is shown in response to user input with respect to another patient shown in a patient list. In this example, the patient is identified as having an "elevated risk of 30 day readmission (0.94)". In response to physician input with respect to this contextual menu, the display can switch to a display of data for another patient. Such a menu can include risk indicators similar to those shown in FIG. 11.

Figure 14:
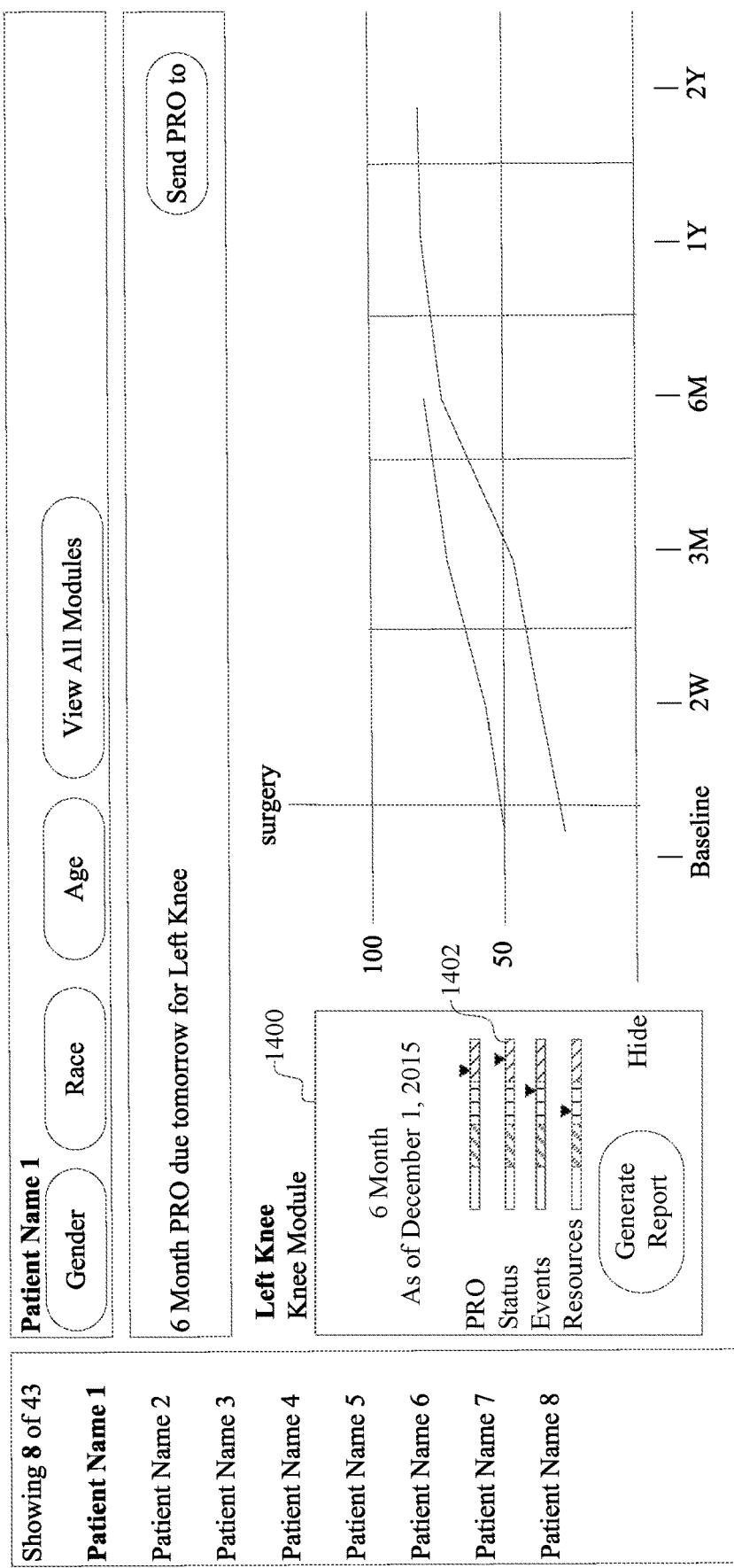
FIG. 14 is an example graphical user interface for use on a client computer showing more detail of use of the interface of FIG. 12.

FIG. 14 is an example graphical user interface for use on a client computer showing more detail of use of the interface of FIG. 12. In response to user input with respect to the displayed outcome score, another graphical representation 1400 of the outcome score is shown. In this representation, a graphical representation of the factor scores, e.g., 1402, are shown. In this example, the factor scores are shown in a range of possible values, with that range shown with different bands of color representing how the factor scores compare to a reference.

FIG. 15 is an example graphical user interface for use on a client computer to provide an administrator's dashboard. An administrator can be an individual that is reviewing data for a patient group but who is not the physician or the patient. In general, such an interface will use and present de-identified and/or aggregated data from the patient data. In this example interface, the administrator has a few categories in which patients may be classified, which are shown as a few modules of a cardiology program. Generally speaking, the dashboard includes a graphical representation 1500 of a patient group. For example a 6 month trailing average of outcome scores for all patients in this category can be computed and displayed. A number of active patients in the category also can be displayed. In response to user input with respect to the representation 1500 of a patient group, the system can transition to a display that generates reports. As an example, a comparison report is shown in FIGS. 16 and 17.

Figure 16:
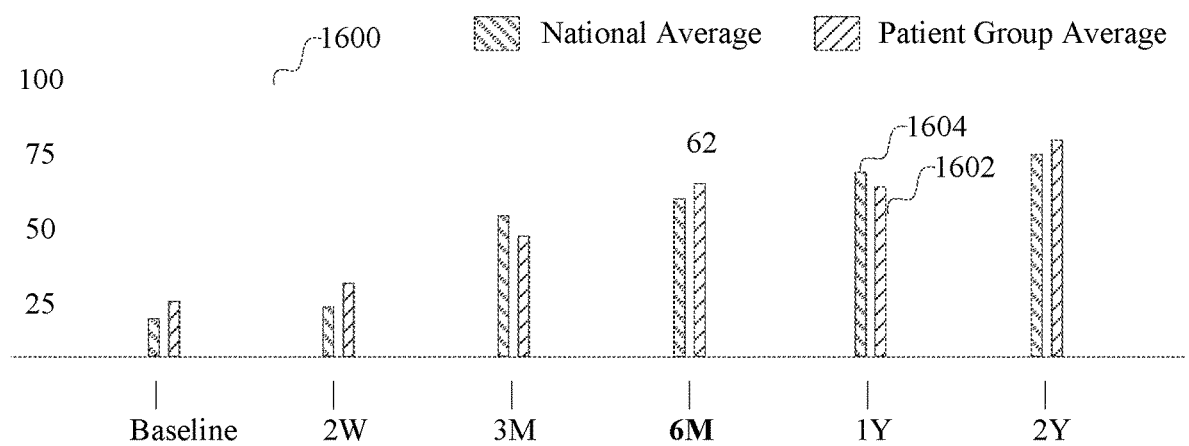
FIG. 16 is an example graphical user interface for use on a client computer to provide a comparison report.

FIG. 16 is an example graphical user interface for use on a client computer to provide a comparison report. This report includes a graphical representation 1600 of a comparison barchart over time. The bars 1602, 1604 represent, respectively, an average patient outcome score (or other score) for a group of patients, and a reference outcome score (or other score), typically for another group of patients, at a given point in time in historical patient data. The reference outcome score can be, for example, a national average, regional average, demographic average or the like. The scores can be risk adjusted and the interface can have a provision for user selection from among different risk adjustment models that apply risk adjustments based on patients' medical data.

Figure 17:
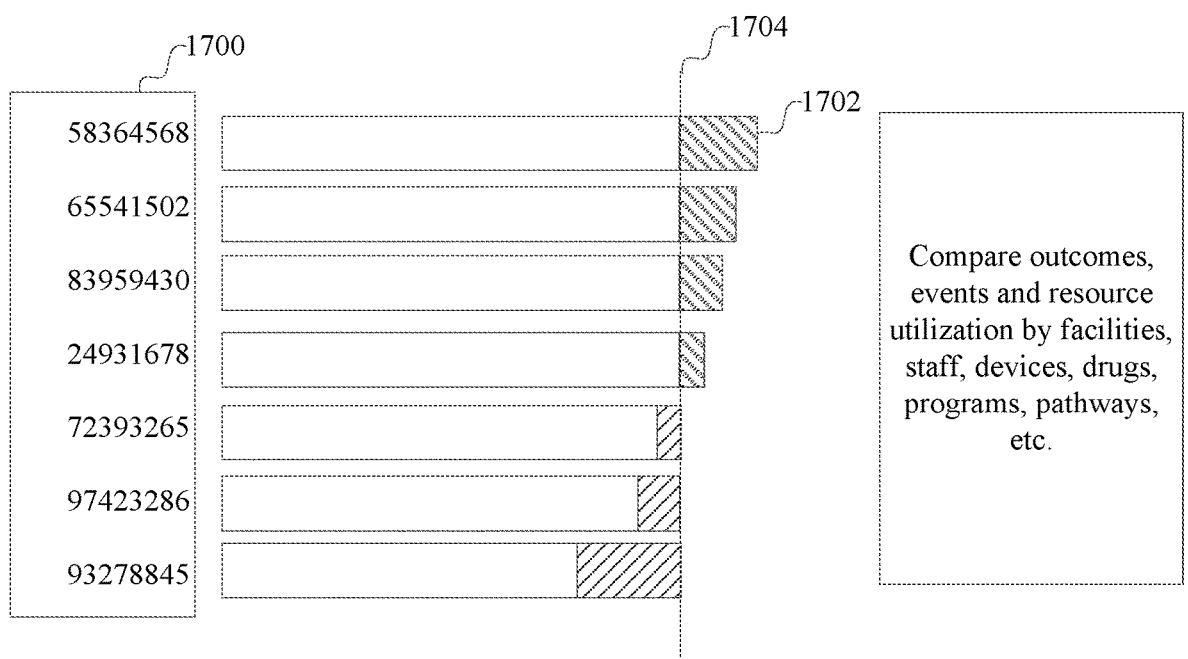
FIG. 17 is an example graphical user interface for use on a client computer to provide another implementation of a comparison report.

Condition scores in FIGS. 16 and 17 can be computed for any group of patients, where the group can be defined using any filtering or searching criteria applied to the patient data. For example, patients can be grouped according to one or more conditions, physicians, treatments, demographic information or any other data in the patient data 102. Within a group of patients, the data as shown in a graph such as FIG. 16, can be further segmented by subgroup at a point in time, and can be further compared using an interface such as shown in FIG. 17.

FIG. 17 is an example graphical user interface for use on a client computer to provide another implementation of a comparison report. Such an interface can be displayed, for example, below the interface of FIG. 16 within the same general display area on the display and interactively changed in response to a selected time point on the interface of FIG. 16. The interface of FIG. 17 illustrates subgroups 1700 of the patient data. For each subgroup, there is a graphical indication of an average score that that subgroup, e.g., 1702 in comparison to a reference 1704, which may represent a national average, group average, other average or an arbitrary reference. The subgroup of the patient data can be based on any data field or combination of data files in the patient data, such as by facility, health care provider or staff, devices, drugs, programs, pathways, or other patient data field by which a group of patients can be segmented into subgroups for which a comparison of interest can be made. The average score presented in the interface can be any of the factor scores, or the outcome score. For example, one can analyze and compare the resource utilization for patients among subgroups based on the physician. As another example, one can analyze patient reported outcomes for patients among subgroups based on drugs prescribed. A wide range of comparisons of factor scores and outcome scores among different segments of patient populations can be presented.

The foregoing description is an example implementation of health care information system. The various computers used in this computer system can be implemented using one or more general purpose computers, such as client computers, server computers and database computers, which can be programmed to implement the functionality such as described in the example implementation. FIG. 6 is a block diagram of a general purpose computer with computer programs providing instructions to be executed by a processor in the general purpose computer. Computer programs on a general purpose computer generally include an operating system and applications. The operating system is a computer program running on the computer that manages access to various resources of the computer by the applications and the operating system. The various resources generally include memory, storage, communication interfaces, input devices and output devices.

Examples of such general purpose computers include, but are not limited to, larger computer systems such as server computers, database computers, desktop computers, laptop and notebook computers, as well as mobile or handheld computing devices, such as a tablet computer, hand held computer, smart phone, media player, personal data assistant, audio and/or video recorder, or wearable computing device.

Figure 6:
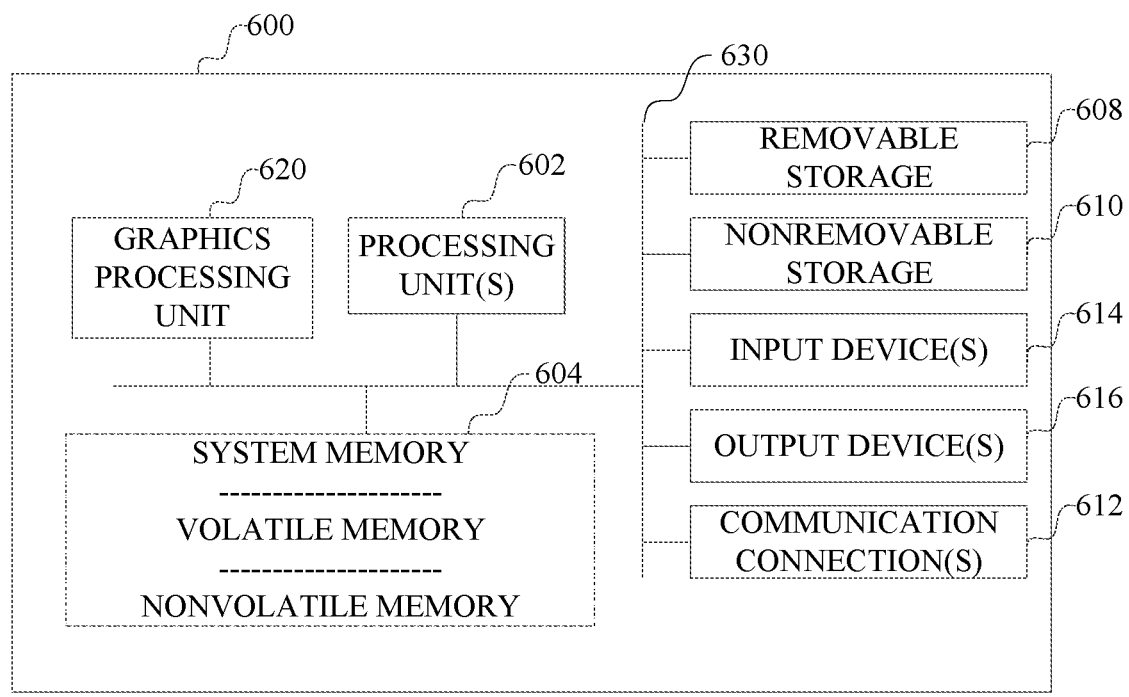
FIG. 6 is a block diagram of an example computer.

With reference to FIG. 6, an example computer 600 includes at least one processing unit 602 and memory 604. The computer can have multiple processing units 602 and multiple devices implementing the memory 604. A processing unit 602 can include one or more processing cores (not shown) that operate independently of each other. Additional co-processing units, such as graphics processing unit 620, also can be present in the computer. The memory 604 may include volatile devices (such as dynamic random access memory (DRAM) or other random access memory device), and non-volatile devices (such as a read-only memory, flash memory, and the like) or some combination of the two, and optionally including any memory available in a processing device. Other memory such as dedicated memory or registers also can reside in a processing unit. This configuration of memory is illustrated in FIG. 6 by dashed line 604. The computer 600 may include additional storage (removable and/or non-removable) including, but not limited to, magnetically-recorded or optically-recorded disks or tape. Such additional storage is illustrated in FIG. 6 by removable storage 608 and non-removable storage 610. The various components in FIG. 6 are generally interconnected by an interconnection mechanism, such as one or more buses 630.

A computer storage medium is any medium in which data can be stored in and retrieved from addressable physical storage locations by the computer. Computer storage media includes volatile and nonvolatile memory devices, and removable and non-removable storage media. Memory 604 and 606, removable storage 608 and non-removable storage 610 are all examples of computer storage media. Some examples of computer storage media are RAM, ROM, EEPROM, flash memory or other memory technology, CD-ROM, digital versatile disks (DVD) or other optically or magneto-optically recorded storage device, magnetic cassettes, magnetic tape, magnetic disk storage or other magnetic storage devices. Computer storage media and communication media are mutually exclusive categories of media.

The computer 600 may also include communications connection(s) 612 that allow the computer to communicate with other devices over a communication medium. Communication media typically transmit computer program instructions, data structures, program modules or other data over a wired or wireless substance by propagating a modulated data signal such as a carrier wave or other transport mechanism over the substance. The term "modulated data signal" means a signal that has one or more of its characteristics set or changed in such a manner as to encode information in the signal, thereby changing the configuration or state of the receiving device of the signal. By way of example, and not limitation, communication media includes wired media such as a wired network or direct-wired connection, and wireless media include any non-wired communication media that allows propagation of signals, such as acoustic, electromagnetic, electrical, optical, infrared, radio frequency and other signals. Communications connections 612 are devices, such as a network interface or radio transmitter, that interface with the communication media to transmit data over and receive data from signals propagated through communication media.

The communications connections can include one or more radio transmitters for telephonic communications over cellular telephone networks, and/or a wireless communication interface for wireless connection to a computer network. For example, a cellular connection, a WiFi connection, a Bluetooth connection, and other connections may be present in the computer. Such connections support communication with other devices, such as to support voice or data communications.

The computer 600 may have various input device(s) 614 such as a various pointer (whether single pointer or multi-pointer) devices, such as a mouse, tablet and pen, touchpad and other touch-based input devices, stylus, image input devices, such as still and motion cameras, audio input devices, such as a microphone. The compute may have various output device(s) 616 such as a display, speakers, printers, and so on, also may be included. All of these devices are well known in the art and need not be discussed at length here.

The various storage 610, communication connections 612, output devices 616 and input devices 614 can be integrated within a housing of the computer, or can be connected through various input/output interface devices on the computer, in which case the reference numbers 610, 612, 614 and 616 can indicate either the interface for connection to a device or the device itself as the case may be.

An operating system of the computer typically includes computer programs, commonly called drivers, which manage access to the various storage 610, communication connections 612, output devices 616 and input devices 614. Such access generally includes managing inputs from and outputs to these devices. In the case of communication connections, the operating system also may include one or more computer programs for implementing communication protocols used to communicate information between computers and devices through the communication connections 612.

Any of the foregoing aspects may be embodied as a computer system, as any individual component of such a computer system, as a process performed by such a computer system or any individual component of such a computer system, or as an article of manufacture including computer storage in which computer program instructions are stored and which, when processed by one or more computers, configure the one or more computers to provide such a computer system or any individual component of such a computer system.

Each component (which also may be called a "module" or "engine" or the like), of a computer system such as described herein, and which operates on one or more computers, can be implemented using the one or more processing units of the computer and one or more computer programs processed by the one or more processing units. A computer program includes computer-executable instructions and/or computer-interpreted instructions, such as program modules, which instructions are processed by one or more processing units in the computer. Generally, such instructions define routines, programs, objects, components, data structures, and so on, that, when processed by a processing unit, instruct the processing unit to perform operations on data or configure the processor or computer to implement various components or data structures. A data structure is defined in a computer program and specifies how data is organized in storage, such as in a memory device or a storage device, so that the data can accessed, manipulated and stored.

It should be understood that the subject matter defined in the appended claims is not necessarily limited to the specific implementations described above. The specific implementations described above are disclosed as examples only.

What is claimed is:

The invention claimed is:

1. A computer system, comprising:
   a processing system comprising a processing device and memory;
   computer storage medium accessible by the processing system and storing data structures representing health care information for a plurality of patients, the health care information including, for the plurality of patients, normalized data from a plurality of sources;
   a plurality of classifiers, each classifier representing a respective different category associated with a respective medical condition, from among a plurality of such categories, each classifier comprising computer program instructions that, when processed by the processing system, configure the processing system to be comprising:
   i. an input connected to receive health care information for a patient from the computer storage, and
   ii. an output indicative of the likelihood the health care information for the patient indicates the patient has the medical condition associated with the category represented by the classifier,
   wherein each classifier is based on training a model using a respective machine learning algorithm using a respective training set including at least some of the normalized data from the stored health care information for patients identified as representative of the respective category represented by the classifier;
   wherein the health care information, for each patient in the plurality of patients, comprises at least
   i. for each category in which the patient is classified, respective patient reported outcome data for the patient for the category, wherein the patient reported outcome data comprises data representing quality of life data reported by the patient,
   ii. for each category in which the patient is classified, respective clinical response data for the patient for the category, wherein clinical response data comprises data representing observations made by health care professionals of the patient, and
   iii. events of interest data, wherein the events of interest data comprises data representing occurrences of specified negative events in health of the patient;
   a data input module, comprising computer program instructions that, when processed by the processing system, configure the processing system to receive and store, in the health care information for the patients in the computer storage, data including patient reported outcome data, clinical response data, and events of interest data for patients; and
   an outcome score processing module, comprising computer program instructions that, when processed by the processing system, configure the processing system to be comprising an input connected to the computer storage medium to receive the health care information for the plurality of patients, and an output providing data to the computer storage medium indicative of respective outcome scores for each patient for each of the respective categories in which the patient is classified, the outcome score processing module being configured to, for each patient for each category, compute, and store in the health care information for the patient in the computer storage, the outcome score for the category for the patient using an outcome function defined for the category;

wherein the outcome function for each category is standardized across all patients classified in the category, and wherein the outcome function for each category is based on the clinical response data for the patient for the category, the patient reported outcome data for the patient for the category, and the events of interest data for the patient.

2. The computer system of claim 1, wherein the outcome score is reported on a numeric scale.

3. The computer system of claim 2, wherein the numeric scale is a percentage.

4. The computer system of claim 2, wherein the numeric scale is a range from 0 to an integer multiple of 10.

5. The computer system of claim 1, wherein the outcome function is further based on a survival factor indicating whether the patient has survived up to a point in time.

6. The computer system of claim 5, wherein the outcome function is further based on a resource score indicating resources consumed for health care for the patient.

7. The computer system of claim 6, wherein the outcome function for each category comprises a respective weighted combination of a unified clinical response measurement based on the clinical response data for the patient for the category, a unified patient reported measurement based on the patient reported data for the patient for the category, a unified events of interest measurement based on the events of interest data for the patient, the survival score, and the resource score.

8. The computer system of claim 7, wherein the unified clinical response measurement comprises a function of n clinical response measurements, each normalized on a common scale.

9. The computer system of claim 8, wherein the unified clinical response measurement is computed using a scale of 0-100, where 0 is a worst possible score and 100 is a best possible score.

10. The computer system of claim 7, wherein the unified patient reported outcome measurement for a category comprises a function of n patient reported measurements for the category, each normalized on a common scale.

11. The computer system of claim 10, wherein the unified patient reported outcome measurement is computed using a scale of 0-100 where 0 is a worst possible score and 100 is a best possible score.

12. The computer system of claim 7, wherein the unified events of interest measurement includes an algebraic sum of scores for each of a plurality of events of interest.

13. The computer system of claim 12, wherein each of the events of interest is individually graded for severity using a numerical grading scale with one or more defined clinical criteria.

14. The computer system of claim 13, wherein the unified events of interest measurement is computed using a scale of 0-100 where 0 is a worst possible score and 100 is a best possible score.

15. The computer system of claim 1, wherein the outcome function for each category comprises a respective weight combination of a unified patient reported measurement for the category based on the clinical response data for the patient for the category, a unified clinical response measurement for the category based on the patient reported data for the patient for the category, and a unified events of interest measurement based on the events of interest data for the patient.

16. The computer system of claim 1, further comprising:
a graphical user interface comprising computer program instructions that, when processed by the processing system, configure the processing system to:
access the computer storage medium to retrieve, for a plurality of patients in a category, outcome scores computed for the category for the plurality of patients;
generate a first graphical representation of the outcome scores for the plurality of patients and present the first graphical representation to a user through a display device;
receive from the user an input indicative of a selection of a patient from among the plurality of patients for which the outcomes scores are presented; and
generate a second graphical representation of data for the selected patient and present the second graphical representation to the user through the display device.

17. The computer system of claim 1, further comprising:
a risk calculator, comprising computer program instructions that, when processed by the processing system, configure the processing system to be comprising an input connected to the computer storage medium to receive the health care information for the plurality of patients, and an output providing one or more respective risk factors for each patient to the computer storage.

18. The computer system of claim 17, further comprising:
a graphical user interface comprising computer program instructions that, when processed by the processing system, configure the processing system to:
access the computer storage medium to retrieve, for a plurality of patients in a category, outcome scores computed for the category for the plurality of patients;
access the one or more respective risk factors for the plurality of patients; and
generate a graphical representation of the outcome scores and the one or more respective risk factors for the plurality of patients and present the graphical representation to a user through a display device.

19. The computer system of claim 18, wherein an order of presentation of the graphical representation is based on a relative ranking of outcome scores of the plurality of patients.

20. The computer system of claim 19, wherein the graphical user interface is further configured to receive from the user an input indicative of a selection of a patient based on the one or more respective risk factors for the patient and to generate and present a second graphical representation of data for the selected patient through the display device.

* * * * *